(12) United States Patent
Maddur et al.

(10) Patent No.: US 12,076,009 B2
(45) Date of Patent: Sep. 3, 2024

(54) TISSUE GUIDE FOR CURVED END EFFECTORS

(71) Applicant: Covidien LP, Mansfield, MA (US)

(72) Inventors: Jeevan Shankar Setty Maddur, Bangalore (IN); Shaohui Shi, Shanghai (CN); Sridharan Varadhan, Hyderabad (IN); Xini Zhang, Shanghai (CN); Syed Sarfraz Ahamed, Shanghai (CN); Manojit Hazra, Hyderabad (IN)

(73) Assignee: Covidien LP, Mansfield, MA (US)

( * ) Notice: Subject to any disclaimer, the term of this patent is extended or adjusted under 35 U.S.C. 154(b) by 97 days.

(21) Appl. No.: 17/797,196

(22) PCT Filed: Feb. 3, 2020

(86) PCT No.: PCT/CN2020/074175
§ 371 (c)(1),
(2) Date: Aug. 3, 2022

(87) PCT Pub. No.: WO2021/155483
PCT Pub. Date: Aug. 12, 2021

(65) Prior Publication Data
US 2023/0052972 A1 Feb. 16, 2023

(51) Int. Cl.
*A61B 17/072* (2006.01)

(52) U.S. Cl.
CPC .. *A61B 17/072* (2013.01); *A61B 2017/07221* (2013.01); *A61B 2017/07257* (2013.01)

(58) Field of Classification Search
CPC ... A61B 17/072; A61B 17/105; A61B 17/115; A61B 17/1157; A61B 2017/07221;
(Continued)

(56) References Cited

U.S. PATENT DOCUMENTS

| 1,158,111 A | 10/1915 | Ahlheim |
| 2,891,250 A | 6/1959 | Hirata |

(Continued)

FOREIGN PATENT DOCUMENTS

| CN | 106923874 A | * 7/2017 | ........... A61B 17/072 |
| CN | 107106169 A | 8/2017 | |

(Continued)

OTHER PUBLICATIONS

Japanese Office Action dated Oct. 24, 2023, issued in corresponding JP Appln. No. 2022-547073, 7 pages.

(Continued)

*Primary Examiner* — Stephen F. Gerrity
*Assistant Examiner* — Linda J Hodge
(74) *Attorney, Agent, or Firm* — Carter, DeLuca & Farrell, LLP

(57) ABSTRACT

A surgical stapling instrument includes an elongate body portion defining a longitudinal axis, and an end effector supported on a distal portion of the elongated body portion. The end effector includes a housing having a base portion and a jaw portion, an anvil assembly supported on the jaw portion, and a cartridge assembly releasably supported on the base portion. A tissue guide member is operably secured relative to the cartridge assembly to facilitate alignment of the cartridge assembly through a firing stroke.

14 Claims, 21 Drawing Sheets

(58) Field of Classification Search
CPC .......... A61B 2017/07257; A61B 2017/07271; A61B 2017/07228; A61B 2017/07214
See application file for complete search history.

(56) References Cited

U.S. PATENT DOCUMENTS

| | | |
|---|---|---|
| 3,080,564 A | 3/1963 | Strekopitov et al. |
| 3,252,643 A | 5/1966 | Strekopov et al. |
| 3,269,630 A | 8/1966 | Fleischer |
| 3,275,211 A | 9/1966 | Hirsch et al. |
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,272,002 A * | 6/1981 | Moshofsky .......... A61B 17/072 227/135 |
| 4,273,281 A * | 6/1981 | Smith ................. A61B 17/072 227/152 |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A * | 5/1987 | Green ................. A61B 17/072 227/19 |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | Mckean et al. |
| 5,547,117 A | 8/1996 | Hamblin et al. |
| 5,558,266 A | 9/1996 | Green et al. |
| 5,571,285 A | 11/1996 | Chow et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 7,717,312 B2 | 5/2010 | Beetel |
| 7,731,073 B2 | 6/2010 | Wixey et al. |

(56) References Cited

U.S. PATENT DOCUMENTS

| | | |
|---|---|---|
| 7,735,704 B2 | 6/2010 | Bilotti |
| 7,766,207 B2 | 8/2010 | Mather et al. |
| 7,810,690 B2 | 10/2010 | Bilotti et al. |
| 7,828,188 B2 | 11/2010 | Jankowski |
| 7,886,953 B2 | 2/2011 | Schwemberger et al. |
| 8,016,176 B2 | 9/2011 | Kasvikis et al. |
| 8,029,520 B2 | 10/2011 | Korvick et al. |
| 8,033,439 B2 | 10/2011 | Racenet et al. |
| 8,070,038 B2 | 12/2011 | Kostrzewski |
| 8,231,041 B2 | 7/2012 | Marczyk et al. |
| 8,292,904 B2 | 10/2012 | Popovic et al. |
| 8,328,064 B2 | 12/2012 | Racenet et al. |
| 8,360,296 B2 | 1/2013 | Zingman |
| 8,424,738 B2 | 4/2013 | Kasvikis |
| 8,499,994 B2 | 8/2013 | D'Arcangelo |
| 8,596,515 B2 | 12/2013 | Okoniewski |
| 8,627,994 B2 | 1/2014 | Zemlok et al. |
| 8,646,673 B2 | 2/2014 | Bilotti et al. |
| 8,757,467 B2 | 6/2014 | Racenet et al. |
| 8,936,185 B2 | 1/2015 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |
| 9,125,651 B2 | 9/2015 | Mandakolathur Vasudevan et al. |
| 9,192,382 B2 | 11/2015 | Kostrzewski |
| 9,192,387 B1 | 11/2015 | Holsten et al. |
| 9,480,474 B2 | 11/2016 | Ji et al. |
| 9,566,066 B2 | 2/2017 | Kasvikis |
| 9,579,102 B2 | 2/2017 | Holsten et al. |
| 9,655,619 B2 | 5/2017 | Zhang et al. |
| 9,662,111 B2 | 5/2017 | Holsten et al. |
| 9,668,736 B2 | 6/2017 | Holsten et al. |
| 9,675,349 B2 | 6/2017 | Holsten et al. |
| 9,675,350 B2 | 6/2017 | Holsten et al. |
| 9,675,356 B2 | 6/2017 | Racenet et al. |
| 9,814,460 B2 | 11/2017 | Kimsey et al. |
| 9,888,923 B2 | 2/2018 | Chen et al. |
| 9,962,159 B2 | 5/2018 | Heinrich et al. |
| 10,004,504 B2 | 6/2018 | Bryant |
| 10,085,754 B2 | 10/2018 | Sniffin et al. |
| 10,194,913 B2 | 2/2019 | Nalagatla et al. |
| 2004/0164123 A1 | 8/2004 | Racenet et al. |
| 2005/0145672 A1* | 7/2005 | Schwemberger .... A61B 17/072 227/176.1 |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2006/0201992 A1 | 9/2006 | Racenet et al. |
| 2007/0187456 A1 | 8/2007 | Viola et al. |
| 2008/0093415 A1* | 4/2008 | Bilotti ............... A61B 17/072 227/180.1 |
| 2009/0302093 A1* | 12/2009 | Kasvikis ............. A61B 17/29 227/176.1 |
| 2010/0048988 A1 | 2/2010 | Pastorelli et al. |
| 2013/0206813 A1 | 8/2013 | Nalagatla |
| 2016/0249914 A1 | 9/2016 | Zhang et al. |
| 2016/0249923 A1 | 9/2016 | Hodgkinson et al. |
| 2016/0270784 A1 | 9/2016 | Wheeler et al. |
| 2016/0270790 A1 | 9/2016 | Jankowski |
| 2016/0270793 A1 | 9/2016 | Carter et al. |
| 2016/0278779 A1 | 9/2016 | Jankowski |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0128149 A1 | 5/2017 | Heinrich et al. |
| 2017/0189022 A1 | 7/2017 | Adams et al. |
| 2017/0238923 A1 | 8/2017 | Holsten et al. |
| 2017/0238924 A1 | 8/2017 | Holsten et al. |
| 2017/0265861 A1 | 9/2017 | Holsten et al. |
| 2018/0008261 A1 | 1/2018 | Racenet et al. |
| 2018/0049739 A1 | 2/2018 | Kasvikis |
| 2018/0153544 A1* | 6/2018 | Maddur Shankarsetty ................. A61B 90/90 |
| 2018/0221024 A1 | 8/2018 | Heinrich et al. |

FOREIGN PATENT DOCUMENTS

| | | | |
|---|---|---|---|
| CN | 108024810 A | 5/2018 | |
| CN | 108472039 A | 8/2018 | |
| CN | 108472040 A | 8/2018 | |
| EP | 666057 A2 * | 8/1995 | ........... A61B 17/072 |
| EP | 3187128 A1 * | 7/2017 | ......... A61B 17/0686 |
| EP | 3329862 A2 | 6/2018 | |
| JP | 2005193034 A | 7/2005 | |
| JP | 2010259792 A | 11/2010 | |

OTHER PUBLICATIONS

International Search Report and Written Opinion dated Oct. 28, 2020, issued in corresponding international application No. PCT/CN2020/074175, 12 pages.

Extended European Search Report dated Dec. 19, 2023, issued in corresponding EP Application No. 20917522, 8 pages.

* cited by examiner

TISSUE GUIDE FOR CURVED END EFFECTORS

CROSS-REFERENCE TO RELATED APPLICATIONS

This is a National Stage Application of PCT/CN2020/074175 under 35 U.S.C. § 371(a) filed on Feb. 3, 2020, the disclosure of which is incorporated herein by reference in its entirety.

FIELD

The present disclosure relates generally to a surgical instrument and, more specifically, to a surgical stapling instrument for clamping, and joining and/or cutting tissue.

BACKGROUND

Surgical stapling instruments used for applying parallel rows of staples through compressed living tissue are well known in the art, and are commonly used, for example, for closure of tissue or organs during surgical procedures for performing anastomoses and/tissue transection or resection. Surgical stapling instruments are often used for occlusion of organs in thoracic and abdominal procedures. Typically, surgical stapling instruments include an anvil assembly, a cartridge assembly for supporting an array of surgical staples, an approximation mechanism for approximating the anvil and cartridge assemblies, and a firing mechanism for ejecting the surgical staples from the cartridge assembly.

The cartridge assembly may include an alignment pin and a tissue guide for retaining tissue between the cartridge and anvil assemblies and for aligning and maintaining alignment between the cartridge and anvil assemblies during approximation and firing of the surgical stapling instrument.

To ensure alignment of the cartridge and the anvil assemblies, it would be beneficial to have a surgical stapling instrument that includes features that restrict unnecessary movement of the cartridge and anvil assemblies and maintain alignment of the cartridge and anvil assembly during actuation of surgical stapling instrument.

SUMMARY

The present disclosure relates to a surgical stapling instrument comprising an elongate body portion defining a longitudinal axis and having a proximal portion and a distal portion and an end effector supported on the distal portion of the elongated body portion. The end effector includes a housing having a base portion and a jaw portion, an anvil assembly supported on the jaw portion, a cartridge assembly releasably supported on the base portion, and a pusher assembly disposed within the base portion of the housing of the end effector. The base portion secured to the distal portion of the elongate body portion and the cartridge assembly including a housing and a tissue guide. The tissue guide being moveable from a retracted position to an advanced position relative to the housing of the cartridge assembly. The pusher assembly is configured to move the tissue guide from the retracted position to the advanced position such that the tissue guide engages the anvil assembly.

In embodiments, the tissue guide includes a feature for engaging the flange.

The present disclosure further relates to a surgical stapling instrument comprising an elongate body portion defining a longitudinal axis and having a proximal portion and a distal portion and an end effector supported on the distal portion of the elongated body portion. The end effector includes a housing having a base portion and a jaw portion, an anvil assembly supported on the jaw portion, and a cartridge assembly releasably supported on the base portion and moveable between a retracted position and an advanced position. The base portion is secured to the distal portion of the elongate body portion. The cartridge assembly includes a tissue contacting surface and a tissue guide extending from the tissue contacting surface. The tissue guide is spaced from the anvil assembly when in the retracted position and is in engagement with the anvil assembly when in the advanced position.

In embodiments, a free end of the tissue guide is sharpened.

The present disclosure relates to a surgical stapling instrument comprising an elongate body portion defining a longitudinal axis and having a proximal portion and a distal portion and an end effector supported on the distal portion of the elongated body portion. The end effector includes a housing having a base portion and a jaw portion, an anvil assembly supported on the jaw portion, a cartridge assembly releasably supported on the base portion, and a tissue guide selectively extendable from the cartridge assembly. The base portion is secured to the distal portion of the elongate body portion. The tissue guide is configured to engage the anvil assembly as the cartridge assembly is secured to the base portion to cause deployment of the tissue guide.

In embodiments, the anvil assembly includes a flange and the tissue guide engages the flange as the cartridge assembly is secured to the base portion.

In addition, the present disclosure relates to a surgical stapling instrument comprising an elongate body portion defining a longitudinal axis and having a proximal portion and a distal portion and an end effector supported on the distal portion of the elongated body portion. The end effector includes a housing having a base portion and a jaw portion, an anvil assembly supported on the jaw portion, a cartridge assembly releasably supported on the base portion, and a tissue guide assembly selectively extendable relative to the cartridge assembly. The base portion includes at least one tab. The tissue guide assembly is configured to engage the at least one tab of the base portion as the cartridge assembly is secured to the base portion to cause deployment of the tissue guide.

In embodiments, the tissue guide assembly includes a tissue guide portion and a base portion. The base portion may define at least one slot for receiving the at least one tab of the base portion. The tissue guide assembly may further include a spring for biasing the tissue guide portion distally relative to the base portion.

The present disclosure relates to a surgical stapling instrument comprising an elongate body portion defining a longitudinal axis and having a proximal portion and a distal portion and an end effector supported on the distal portion of the elongated body portion. The end effector includes a housing having a base portion and a jaw portion, an anvil assembly supported on the jaw portion, a cartridge assembly releasably supported on the base portion, and a tissue guide assembly selectively extendable relative to the cartridge assembly. The tissue guide assembly includes a first member and a second member. The first member telescopes relative to the second member between retracted and extended positions.

The present disclosure further relates to a surgical stapling instrument comprising an elongate body portion defining a longitudinal axis and having a proximal portion and a distal portion and an end effector supported on the distal portion of the elongated body portion. The end effector includes a housing having a base portion and a jaw portion, an anvil assembly supported on the jaw portion, a cartridge assembly releasably supported on the base portion, and a tissue guide assembly selectively extendable relative to the cartridge assembly. The base portion including at least one tab. The tissue guide assembly includes a tissue guide pivotally secured to the cartridge assembly.

In embodiments, the tissue guide is slidably disposed relative to the cartridge assembly.

Further, the present disclosure relates to a surgical stapling instrument comprising an elongate body portion defining a longitudinal axis and having a proximal portion and a distal portion and an end effector supported on the distal portion of the elongated body portion. The end effector includes a housing having a base portion and a jaw portion, an anvil assembly supported on the jaw portion, a cartridge assembly releasably supported on the base portion, and a tissue guide assembly selectively extendable relative to the cartridge assembly. The base portion includes at least one tab. The tissue guide assembly is configured to engage the at least one tab of the base portion as the cartridge assembly is secured to the base portion to cause deployment of the tissue guide.

The present disclosure relates to a surgical stapling instrument comprising an elongate body portion defining a longitudinal axis and having a proximal portion and a distal portion and an end effector supported on the distal portion of the elongated body portion. The end effector includes a housing having a base portion and a jaw portion, an anvil assembly supported on the jaw portion, a cartridge assembly releasably supported on the base portion, and a tissue guide selectively extendable relative to the cartridge assembly. The base portion includes at least one tab. The tissue guide is configured to engage at least one of the anvil assembly or the base portion as the cartridge assembly is secured to the base portion.

In embodiments, the tissue guide includes a snap feature and the base portion defines an opening for receiving the snap feature. The tissue guide may include a bent portion and the base portion may define an opening for receiving the bent portion.

The present disclosure relates to a surgical stapling instrument comprising an elongate body portion defining a longitudinal axis and having a proximal portion and a distal portion and an end effector supported on the distal portion of the elongated body portion. The end effector includes a housing having a base portion and a jaw portion, an anvil assembly supported on the jaw portion, a cartridge assembly releasably supported on the base portion, a tissue guide assembly selectively extendable relative to the cartridge assembly, and a clamping member disposed within the housing and moveable between a retracted position and an advanced position. The base portion includes at least one tab. The tissue guide assembly may include a tissue guide and a bushing slidably received about the tissue guide. Movement of the clamping member from the retracted position to the advance position may advance the bushing about the tissue guide.

BRIEF DESCRIPTION OF THE DRAWINGS

Various embodiments of the presently disclosed surgical stapling instrument are disclosed herein with reference to the drawings, wherein.

DETAILED DESCRIPTION

Figure 1:
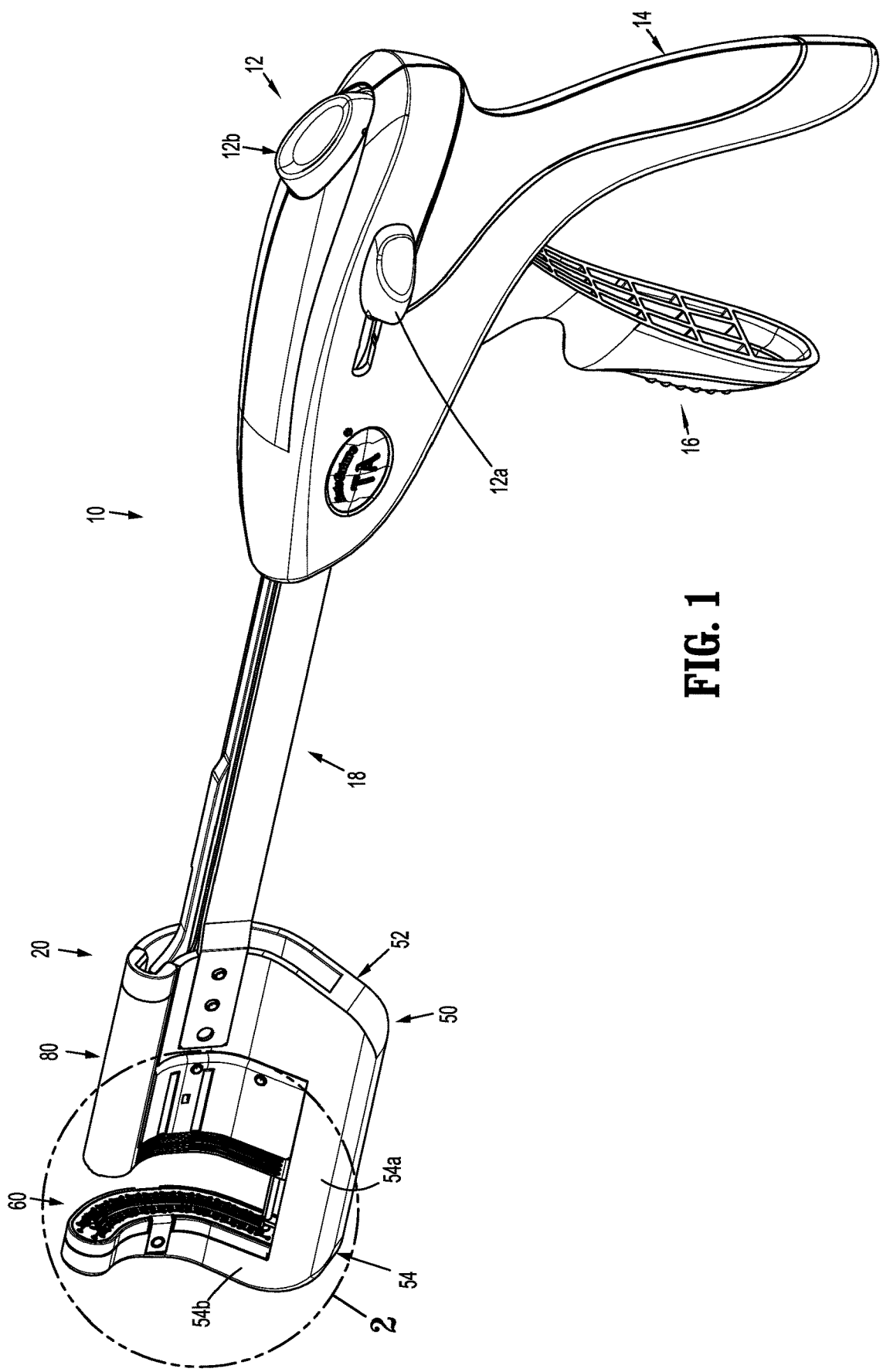
FIG. 1 is a perspective view a surgical stapling instrument with an end effector including a removable cartridge assembly having tissue guide according to an exemplary embodiment of the present disclosure.
Figure 2:
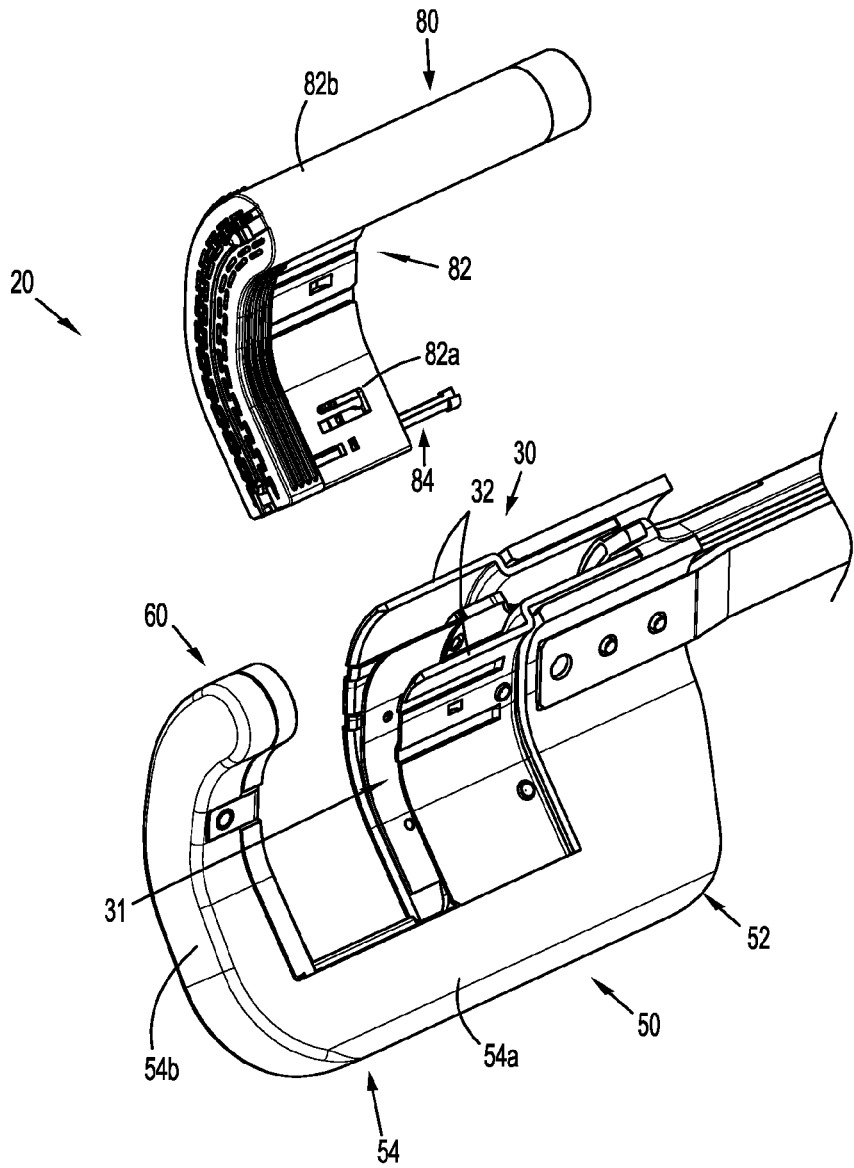
FIG. 2 is an enlarged view of the area of detail indicated in FIG. 1 with the end effector in the open position and a removable cartridge assembly separated from the end effector.

Embodiments of the presently disclosed replaceable cartridge assembly for surgical stapling instruments are described in detail with reference to the drawings, wherein like reference numerals designate corresponding elements in each of the several views. In the drawings and the description that follow, the term "proximal" refers to the end of the surgical stapling instrument that is closer to the clinician, whereas the term "distal" refers to the end of the surgical stapling instrument that is farther from the clinician. In addition, the term "clinician" is used generally to refer to medical personnel including doctors, nurses, and support personnel.

It should be appreciated that the instruments described and illustrated herein are configured to fire surgical staples against an anvil surface; however, aspects of the present disclosure are equally applicable with other forms of staples, fasteners, clips, as well as two part fasteners, made of metallic and/or polymeric materials.

Embodiments of the presently disclosed surgical stapling instruments include a curved end effector having a curved anvil assembly and a curved cartridge assembly. It is envisioned that the aspects of the present disclosure may be suitable for use with surgical stapling instruments having linear end effectors.

With initial reference to FIG. 1, an exemplary embodiment of the presently disclosed surgical stapling instrument is shown generally as stapling instrument 10. The stapling instrument 10 includes a body 12 defining a stationary handle 14, a pivotable trigger 16 movable relative to the stationary handle 14, an elongated central body portion 18 extending from the body 12, and an end effector 20 disposed on a distal end of the elongated central body portion 18. The end effector 20 of the stapling instrument 10 includes an anvil assembly 60 and a replaceable cartridge assembly 80.

A thumb button 12a is slidably positioned on each side of the body 12 of the stapling instrument 10. The thumb buttons 12a are movable to manually advance an alignment pin 86 (FIG. 4) slideably disposed within the replaceable cartridge assembly 80. A release button 12b is positioned on the proximal end of body 12 of the stapling instrument 10 and is depressible to allow the replaceable cartridge assembly 80 to return from an approximated position (not shown) disposed adjacent to the anvil assembly 60 (FIG. 1) to an open position spaced from the anvil assembly 60.

The stapling instrument 10 will be described to the extent necessary to fully disclose aspects of the present disclosure. For a detailed description of the internal structure and function of an exemplary surgical stapling instrument, please refer to commonly owned U.S. Pat. No. 6,817,508 ("the '508 patent"), and commonly owned U.S. Pat. App. Pub. No. 2018/0153544 ("the '544 publication"), the contents of which are incorporated by reference herein in their entireties.

With reference to FIGS. 2-6, the end effector 20 of the stapling instrument 10 (FIG. 1) includes a frame 50 having a base portion 52 and an L-shaped jaw portion 54 extending from the base portion 52. The L-shaped jaw portion 54 includes a longitudinal portion 54a and a transverse portion 54b. The anvil assembly 60 is supported on the transverse portion 54b of the jaw portion 54 of the frame assembly 50 and the cartridge assembly 80 is releasably supported within a head portion 32 of clamp slide members 30 within the base portion 52 of the frame assembly 50.

The base portion 52 and the transverse portion 54b of the jaw portion 54 of the frame assembly 50 of the end effector 20 are curved. In embodiments, the base portion 52 and the transverse portion 54b of the jaw portion 54 of the frame assembly 50 of the end effector 20 are substantially J-shaped although other curved and linear configurations are also envisioned. In embodiments, the end effector 20 includes a first radius of curvature and a second radius of curvature. The first and second radii of curvature may be increased or decreased to suit a particular procedure and/or to facilitate access to a particular body cavity or location within a body cavity. In some embodiments, the end effector 20 is formed by a plurality of substantially linear sections that are connected to each other to define a curved-like configuration. Each of the anvil assembly 60 and the cartridge assembly 80 include a curved configuration corresponding to the curved configuration of the frame assembly 50 of the end effector 20.

In embodiments, a pusher assembly 56 (FIG. 6) is operably disposed within the base portion 52 of the end effector 20. The pusher assembly 56 includes a pusher pin 56a, a pusher member 56b mounted on a distal portion of the pusher pin 56a, and a spring 56c received about the pusher pin 56a for biasing the pusher pin 56a distally. As described in the '544 publication, the pusher pin 56a is maintained in a retracted position by a lock member (not shown) of an interlock assembly (not shown). Loading of the replaceable cartridge assembly 80 within the frame assembly 50 of the end effector 20 depresses the lock member, thereby releasing the pusher pin 56a. As described below, the pusher member 56b on the pusher pin 56a engages a tissue guide 84, causing advancement of the tissue guide 84 into engagement with the anvil assembly 60.

The head portions 32 (FIG. 2) of the clamp slide members 30 of stapling instrument 10 support the replaceable cartridge assembly 80 and are slidably supported within the base portion 52 of the frame assembly 50 of the end effector 20. As disclosed in the '544 publication, the clamp slide members 30 advance in response to actuation of the trigger 16 (FIG. 1) of the stapling instrument 10 (FIG. 1) to cause advancement of the replaceable cartridge assembly 100 relative to the anvil assembly 60. The head portions 32 of the clamp slide members 30 define a channel 31 configured to releasably support the replaceable cartridge assembly 80. For a detailed description of the structure and operation of an exemplary end effector, please refer to the '544 publication.

The cartridge assembly 80 will only be described to the extent necessary to fully disclose the aspects of the present disclosure. For a detailed description of the structure and operation of an exemplary pusher assembly, please refer to the '544 publication.

Figure 4:
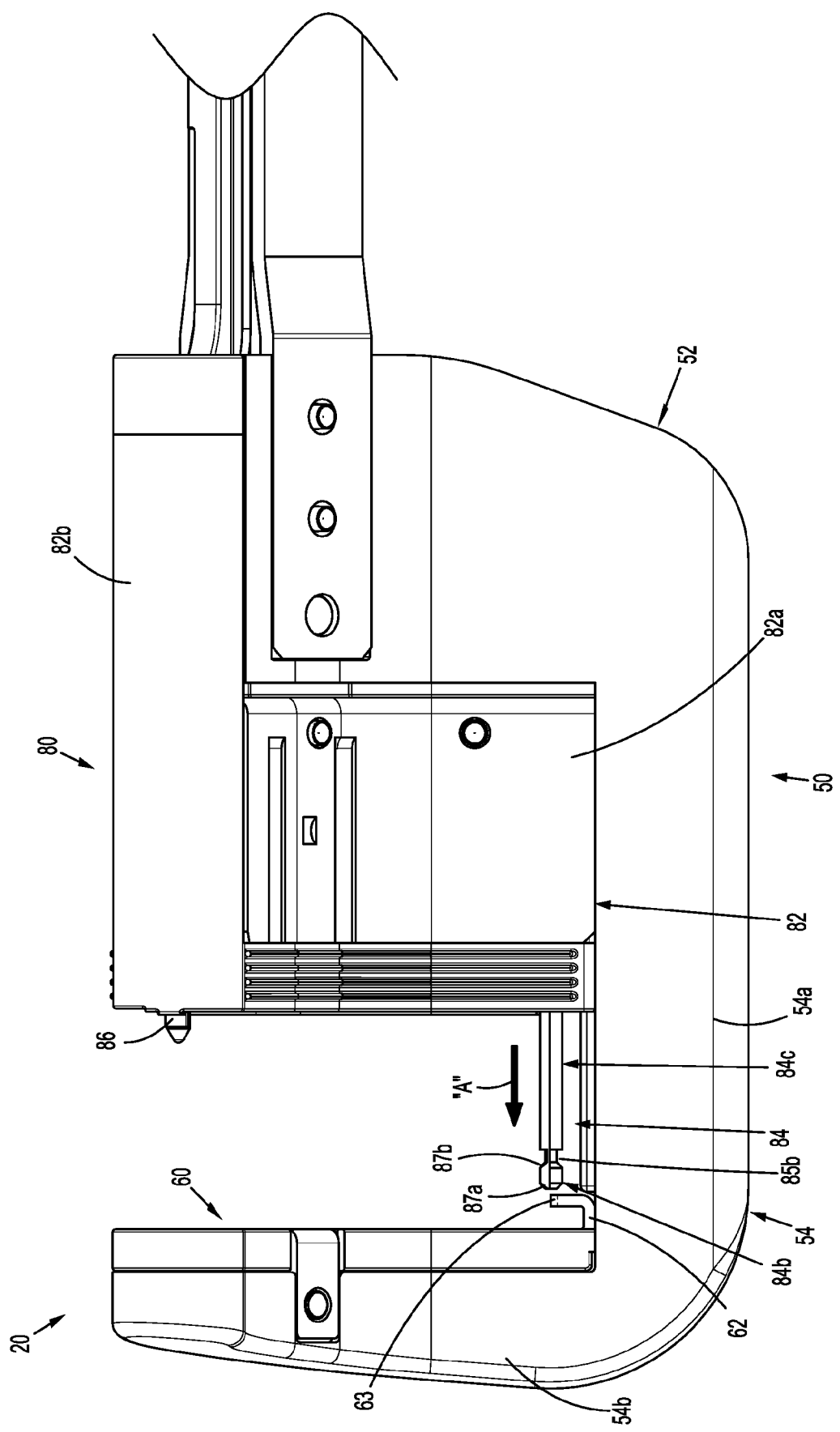
FIG. 4 is an enlarged side view of the end effector shown in FIG. 2 with the tissue guide member in a partially advanced position.
Figure 5:
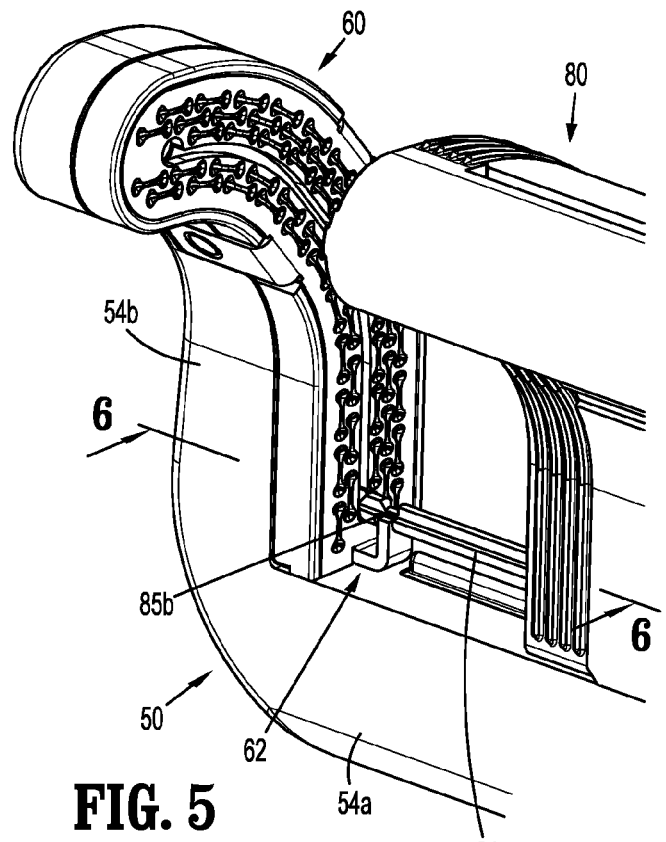
FIG. 5 is a perspective view of a portion of the end effector shown in FIG. 2 with the tissue guide member in an advanced position.
Figure 6:
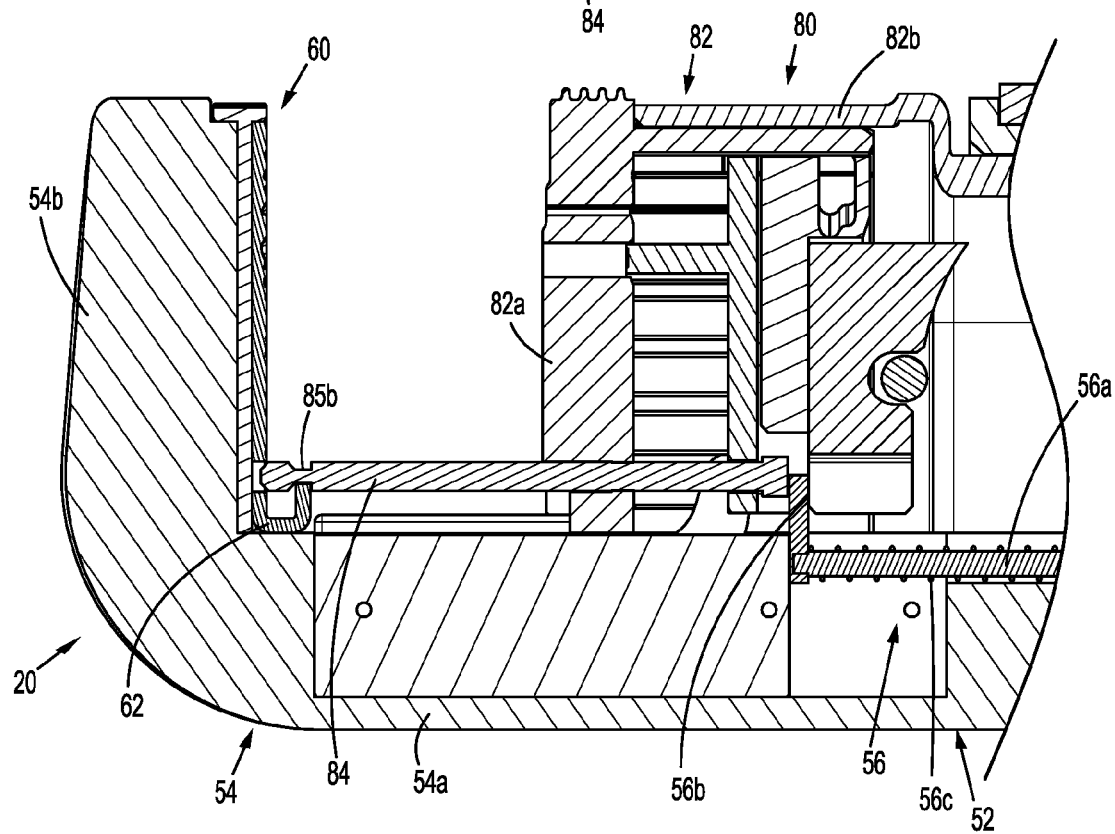
FIG. 6 is a cross-sectional side view taken along line 6-6 shown in FIG. 5.

The replaceable cartridge assembly 80 of the stapling instrument 10 includes a housing 82 having a base portion 82a supporting the tissue guide 84 and an alignment pin retaining portion 82a supporting an alignment pin 86 (FIG. 4). The base portion 82a defines a plurality of staple receiving pockets 82a that support a plurality of staples (not shown). As described above, when the replaceable cartridge assembly 80 is loaded within the frame 50 of the end effector 20, the pusher assembly 56 is activated to cause a distal advancement of the tissue guide 84 (FIG. 6). As disclosed in the '544 publication, prior to or during actuation of the stapling instrument 10, the alignment pin 86 (FIG. 4) is advanced into the anvil assembly 60 to capture tissue between the anvil assembly 60 and the replaceable cartridge assembly 80. The tissue guide 84 and the alignment pin 86 operate together to facilitate and maintain alignment of the replaceable cartridge assembly 80 with the anvil assembly 60 during actuation of the stapling instrument 10.

Although shown and described as including the pusher assembly 56 (FIG. 6), it is envisioned that the stapling instrument 10 may include alternative means for advancing the tissue guide 84. For example, an alignment pin deployment member (not shown) configured for deploying the alignment pin 86, as described in the '544 publication, may be modified to advance the tissue guide 84 simultaneously with the alignment pin 86.

Figure 3:
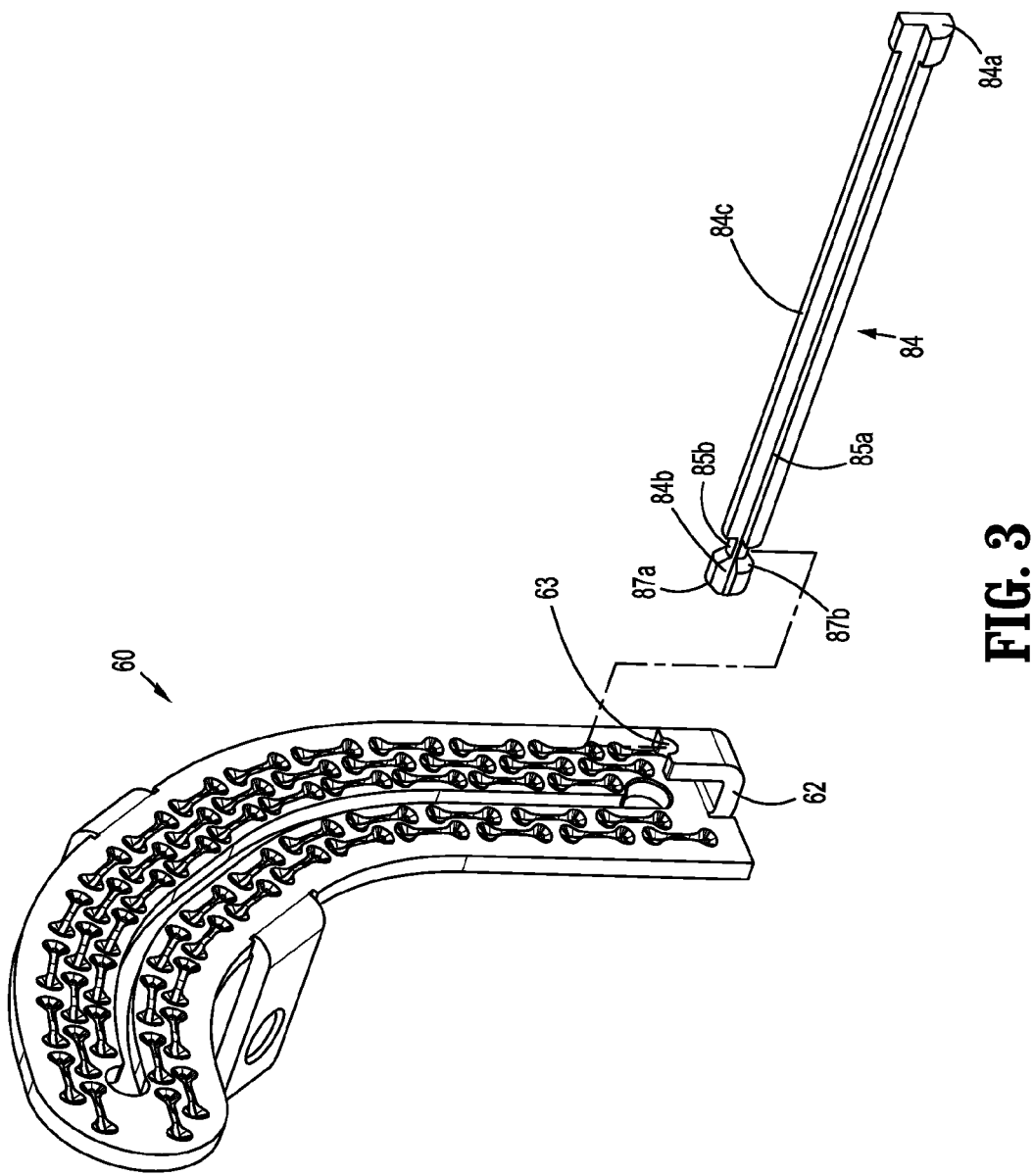
FIG. 3 is a perspective view of an anvil assembly and a tissue guide member of the end effector shown in FIG. 2.

With particular reference to FIG. 3, the tissue guide 84 of the replaceable cartridge assembly 80 includes a proximal engagement portion 84a, a distal head portion 84b, and an elongate body portion 84c extending between the proximal engagement portion 84a and the distal head portion 84b. A longitudinal groove 85a extends the length of the tissue guide 84 for maintaining the rotational orientation of the tissue guide 84 relative to the replaceable cartridge assembly 80 during actuation of the stapling instrument 10. A notch 85b is disposed between the distal head portion 84b and the elongate body portion 84c. The notch 85b accommodates an L-shaped protrusion 62 extending from the anvil assembly 60. As described below, the L-shaped protrusion 62 releasably retains the tissue guide 84 in an extended position (FIG. 6). In embodiments, the distal head portion 84b includes tapered first and second ends 87a, 87b to facilitate engagement and disengagement, respectively, of the distal head portion 84b of the tissue guide 84 with the L-shaped protrusion 62 of the anvil assembly 60. In some embodiments, and as shown, the L-shaped protrusion 62 may define a notch or cutout 63 to facilitate engagement of the distal head portion 84b of the tissue guide 84 with the L-shaped protrusion 62.

Figure 7:
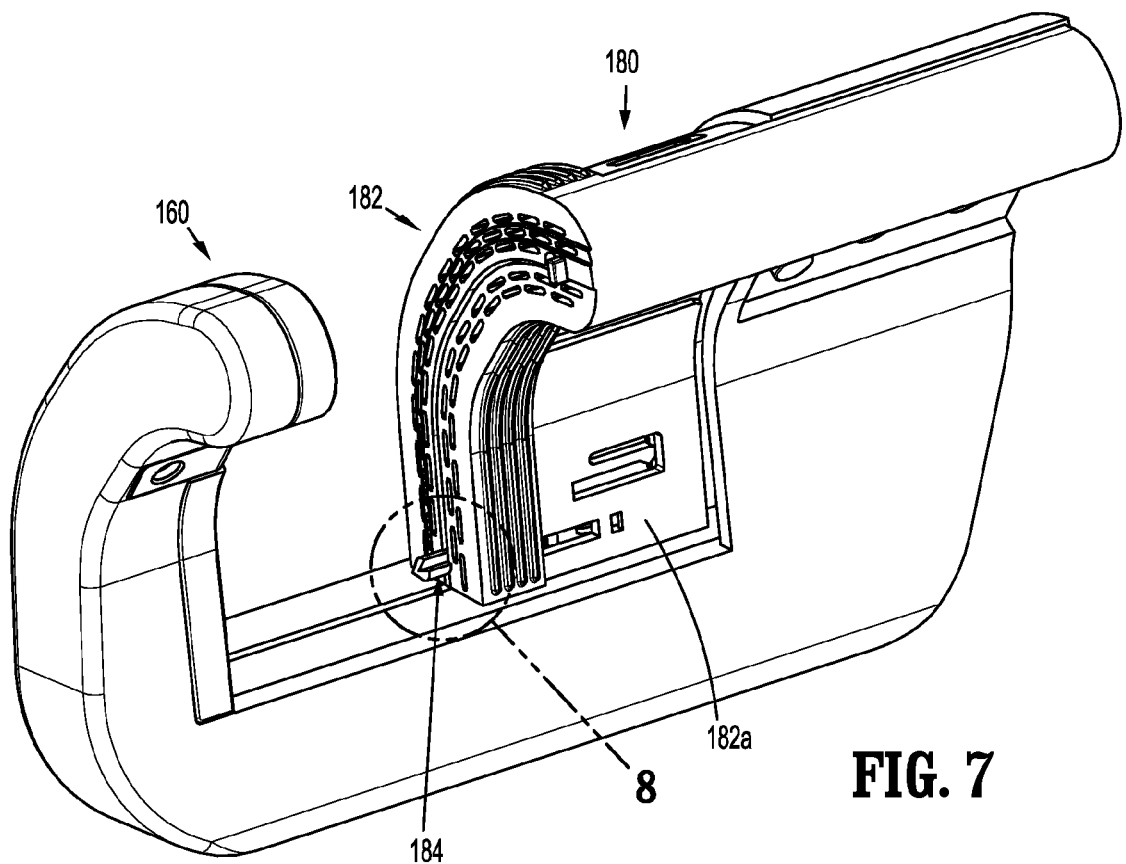
FIG. 7 is a perspective view of an end effector according to another exemplary embodiment of the present disclosure in an open position.
Figure 8:
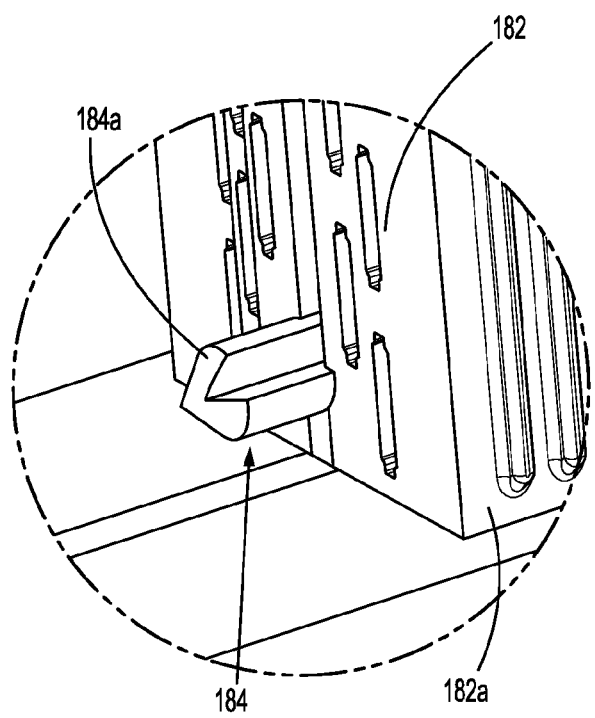
FIG. 8 is an enlarged view of the area of detail indicated in FIG. 7.

With reference to FIGS. 7 and 8, in an alternative embodiment of the present disclosure, a replaceable cartridge assembly 180 includes a tissue guide 184. The replaceable cartridge assembly 180 is substantially similar to the replaceable cartridge assembly 80 described hereinabove, and therefore will only be described in detail as relates to the differences therebetween.

The tissue guide 184 of the replaceable cartridge assembly 180 extends distally from a base portion 182a of a housing 182 of the replaceable cartridge assembly 180 is fixed to the base portion 182a. The tissue guide 184 includes a tissue piercing tip 184a. During operation of the stapling instrument 10 (FIG. 1), the tissue guide 184 is configured to pierce tissue (not shown) retained between the replaceable cartridge assembly 180 and the anvil assembly 60. Engagement of the tissue guide 184 with the anvil assembly 160 during approximation of the replaceable cartridge assembly 180 and the anvil assembly 160 facilitates alignment of the replaceable cartridge assembly 180 with the anvil assembly 160.

Figure 9:
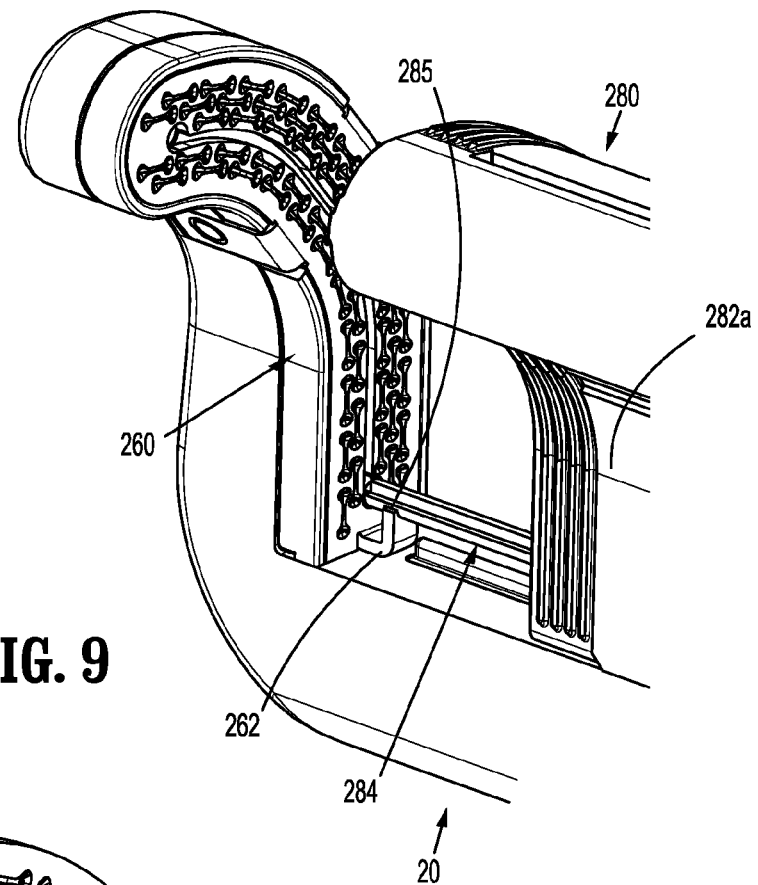
FIG. 9 is a perspective view of an end effector including an anvil assembly and a removable cartridge assembly having a tissue guide member according to another exemplary embodiment of the present disclosure.
Figure 10:
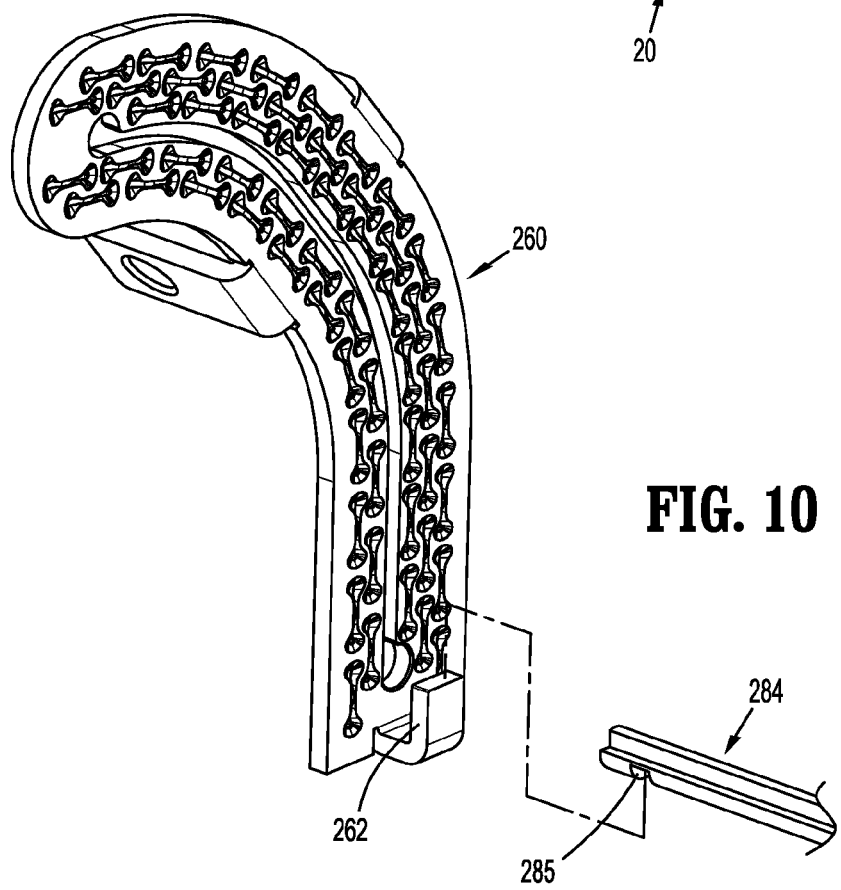
FIG. 10 is a perspective view of the anvil assembly and the tissue guide member of the end effector shown in FIG. 9.
Figure 11:
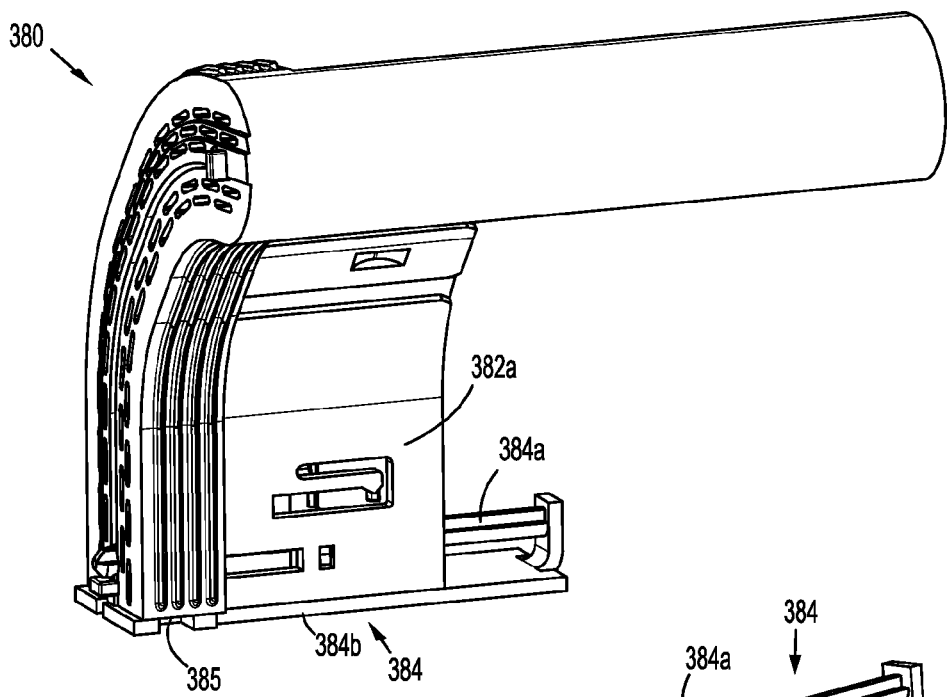
FIG. 11 is a perspective front view of a removable cartridge assembly according to the present disclosure with a tissue guide assembly in a retracted position.
Figure 12:
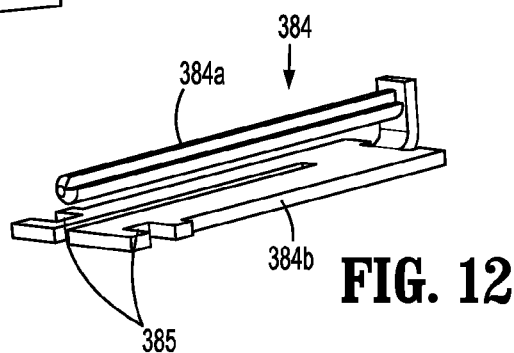
FIG. 12 is a perspective view of a tissue guide assembly of the removable cartridge assembly shown in FIG. 11.

Referring now to FIGS. 9 and 10, in another embodiment of the present disclosure, a replaceable cartridge assembly 280 includes a tissue guide 284. The replaceable cartridge assembly 280 is substantially similar to the replaceable cartridge assembly 180 described hereinabove, and therefore will only be described in detail as relates to the differences therebetween.

The tissue guide 284 of the replaceable cartridge assembly 280 includes a notch 285. The notch 285 is configured to receive a portion of an L-shaped projection 262 extending from an anvil assembly 260 to releasable retain the tissue guide 284 in an extended position (FIG. 9). The tissue guide 284 is configured such that during initial loading of the replaceable cartridge assembly 280 within the frame 50 (FIG. 9) of the end effector 20, the tissue guide 284 engages the L-shaped projection 262. As the replaceable cartridge assembly 280 is moved to a fully loaded position within the frame 50 (FIG. 1), i.e., slid proximally towards the body 12 (FIG. 1) of the stapling instrument 10, the tissue guide 284 extends from the body portion 282a of the replaceable cartridge assembly 280 to maintain engagement with the L-shaped projection 262 of the anvil assembly 260.

With reference now to FIGS. 11-15, in another embodiment of the present disclosure, an end effector 320 (FIG. 12) includes a replaceable cartridge assembly 380 having a tissue guide member 384. The end effector 320 and the replaceable cartridge assembly 380 are substantially similar to the end effector and the replaceable cartridge assemblies described hereinabove, and will only be described in detail as relates to the differences therebetween.

The tissue guide member 384 of the replaceable cartridge assembly 380 includes a tissue guide portion 384a and a base portion 384b. The tissue guide portion 384a extends parallel to the base portion 384b and may be integrally formed, as shown, or may be formed separately and secured together in any suitable manner. The tissue guide member 384 is slidable secured to a base portion 382a of the replaceable cartridge assembly 380. The base portion 384b of the tissue guide member 384 defines a pair of opposed cutouts 385 (FIG. 13) configured to receive a pair of opposed tabs 355 formed on a transverse portion 354b of a jaw portion 354 of a frame assembly 350 of the end effector 320.

Figure 13:
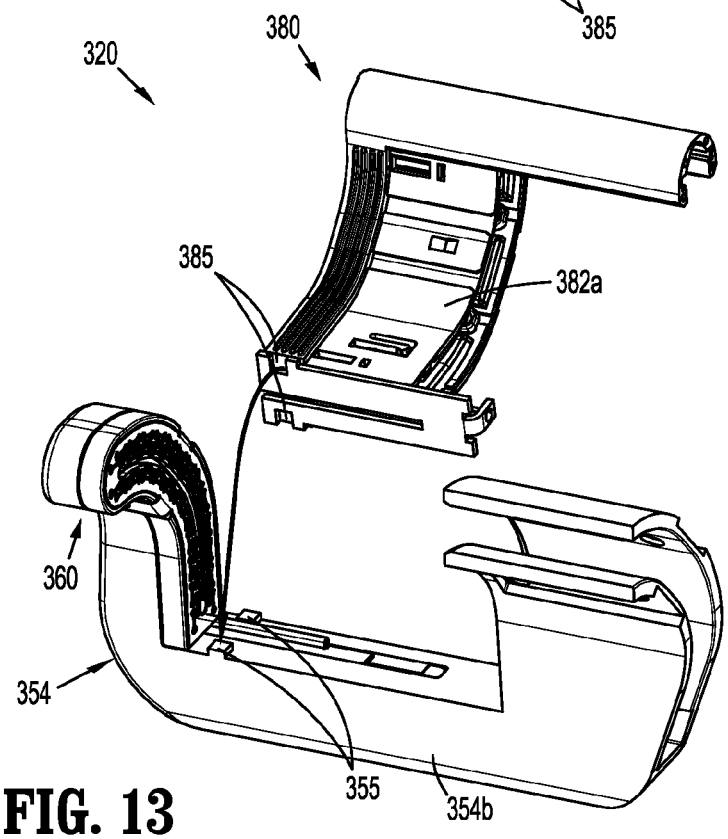
FIG. 13 is a perspective view of an end effector according to the present disclosure prior to loading of the removable cartridge assembly shown in FIG. 11.

With particular reference to FIG. 13, when the replaceable cartridge assembly 380 is partially loaded into the frame assembly 350 of the end effector 320, the opposed tabs 355 on the transverse portion of the jaw portion 354 of the end effector 320 are received within the opposed cutouts 385 in the base portion 384b of the tissue guide member 384.

Figure 14:
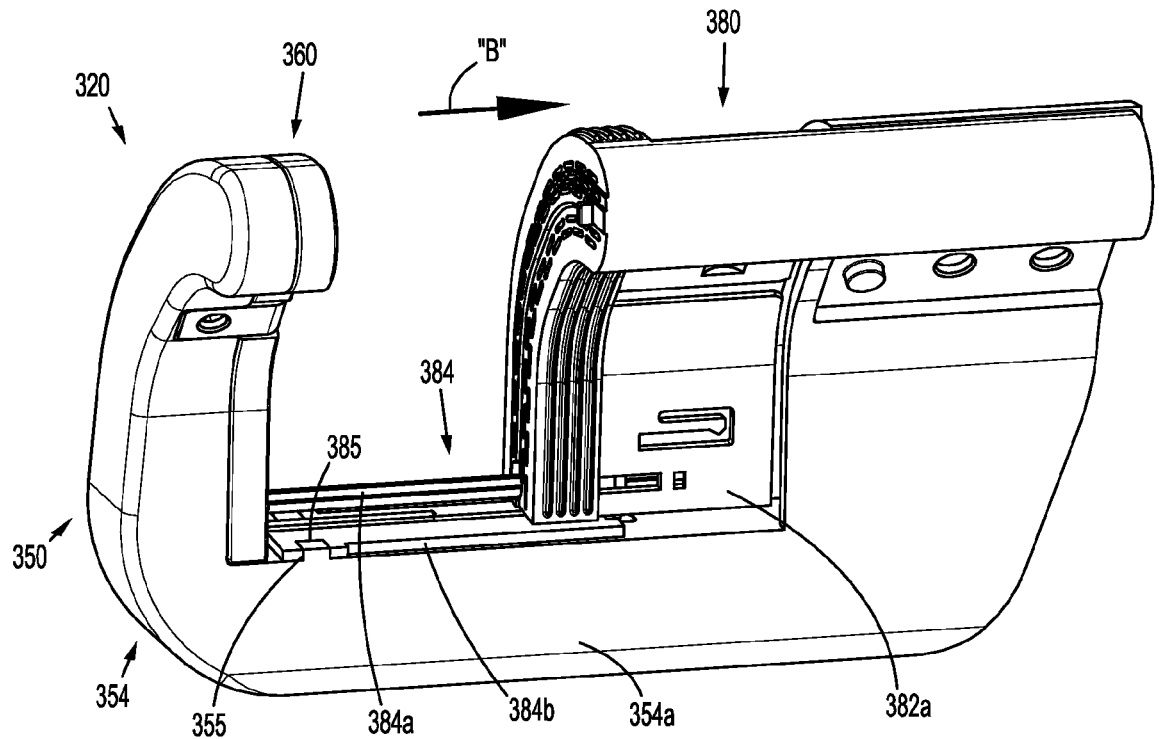
FIG. 14 is a perspective view of the end effector shown in FIG. 13 in an open position.

As the replaceable cartridge assembly 380 is slid into the fully loaded position (FIG. 14), in the direction indicated by arrow "B" shown in FIG. 14, the tissue guide member 384 of the replaceable cartridge assembly 380 remains fixed relative to the transverse portion 354b of a jaw portion 354 of a frame assembly 350 of the end effector 320.

Figure 15:
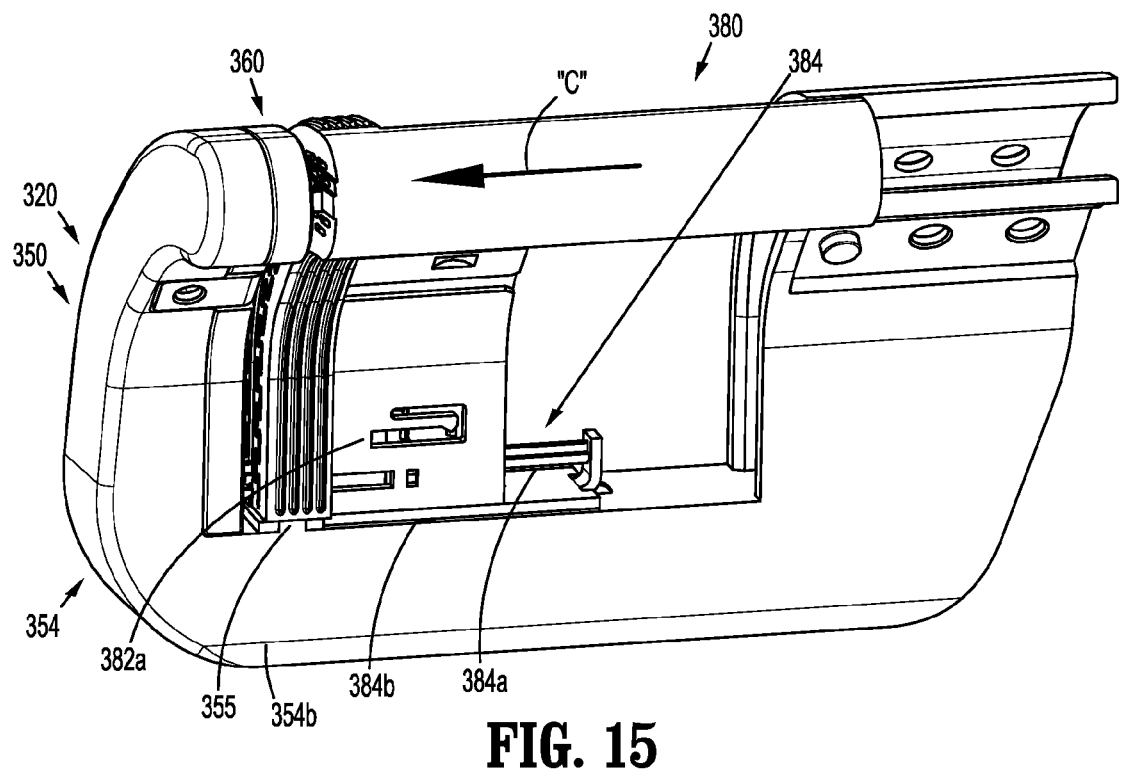
FIG. 15 is a perspective view of the end effector shown in FIG. 13 in a closed position.

With particular reference to FIG. 15, during approximation of the replaceable cartridge assembly 380 relative to an anvil assembly 360 in the direction indicated by arrow "C" as the stapling instrument 10 is actuated, the tissue guide member 384 facilitates and maintains alignment of the replaceable cartridge assembly 380 relative to the anvil assembly 360.

Figure 16:
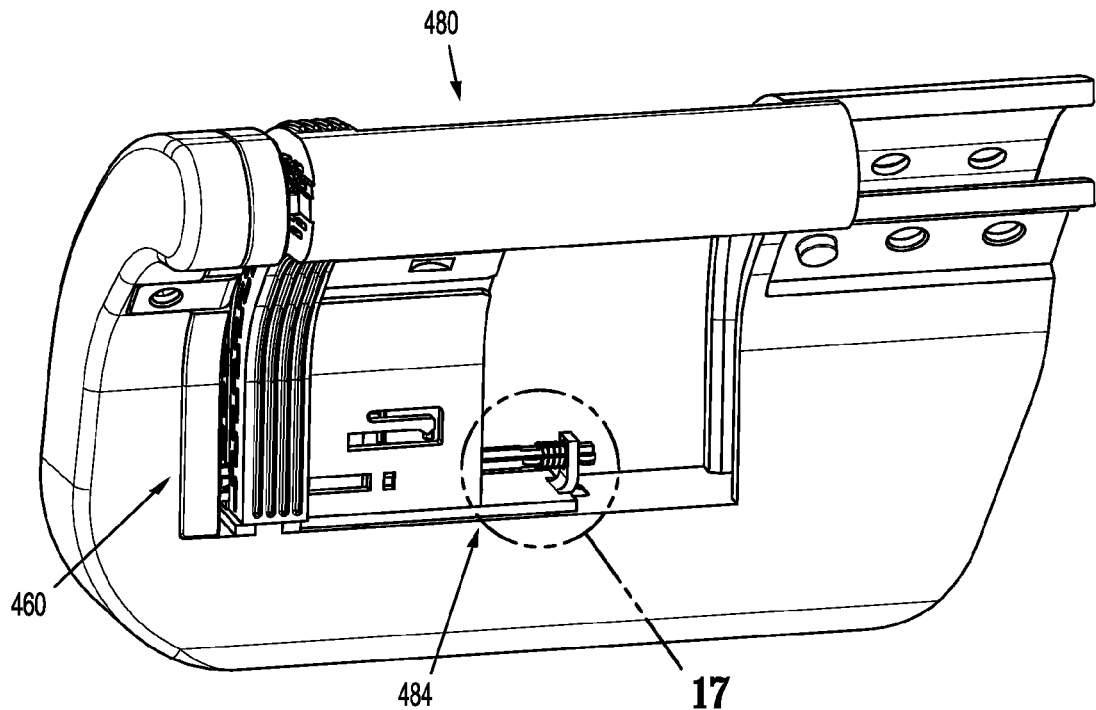
FIG. 16 is a perspective view of an end effector including a removable cartridge assembly having a tissue guide assembly according to another exemplary embodiment of the present disclosure.
Figure 17:
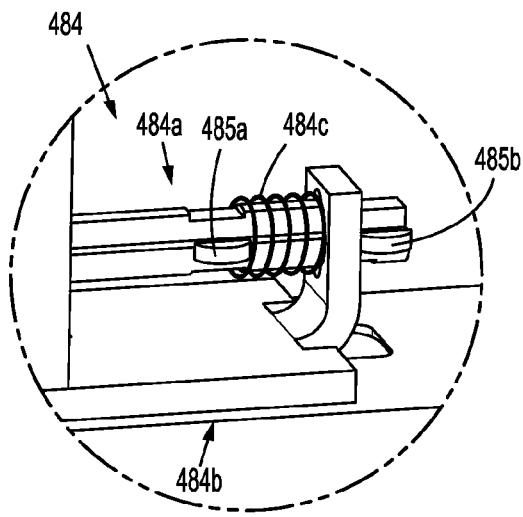
FIG. 17 is an enlarged view of the area of detail indicated in FIG. 16.
Figure 18:
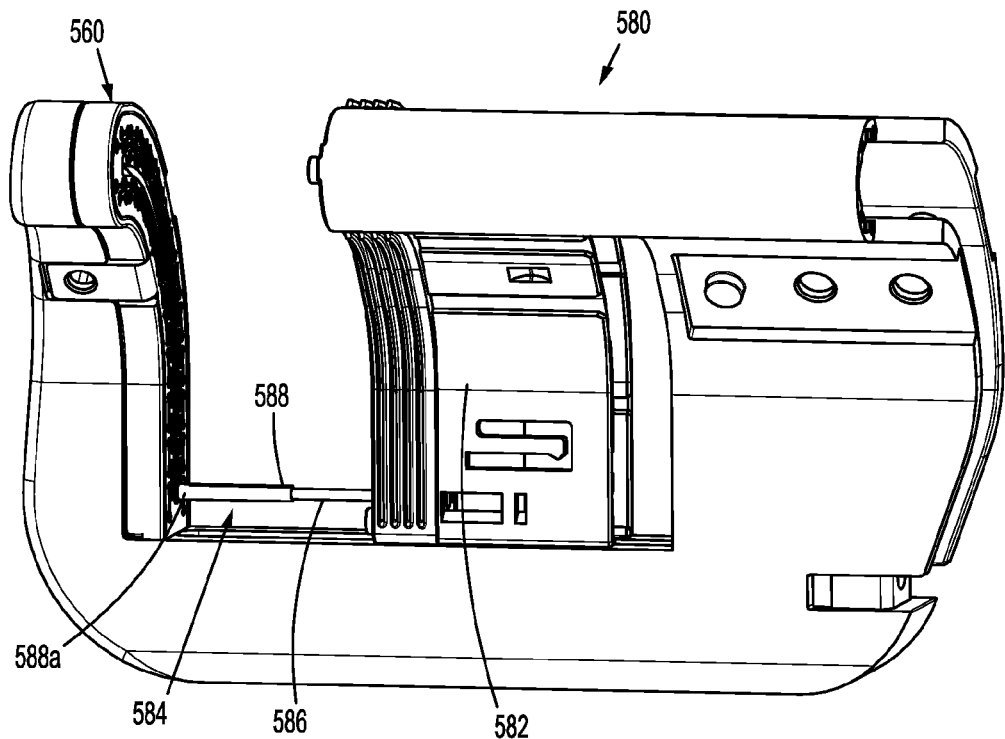
FIG. 18 is a perspective view of an end effector including a removable cartridge assembly having a tissue guide assembly according to another exemplary embodiment of the present disclosure.
Figure 19:
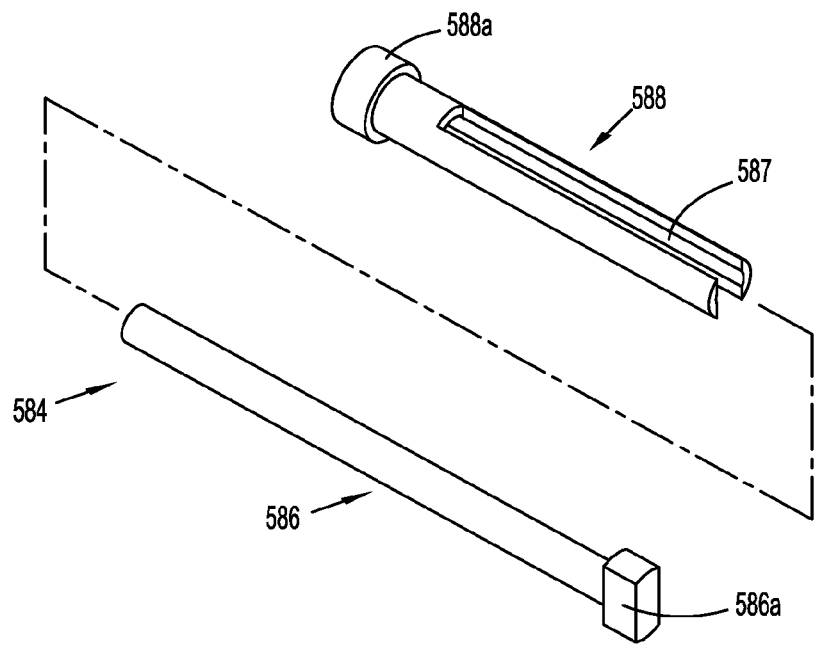
FIG. 19 is a perspective view of the tissue guide assembly shown in FIG. 18, with parts separated.
Figure 20:
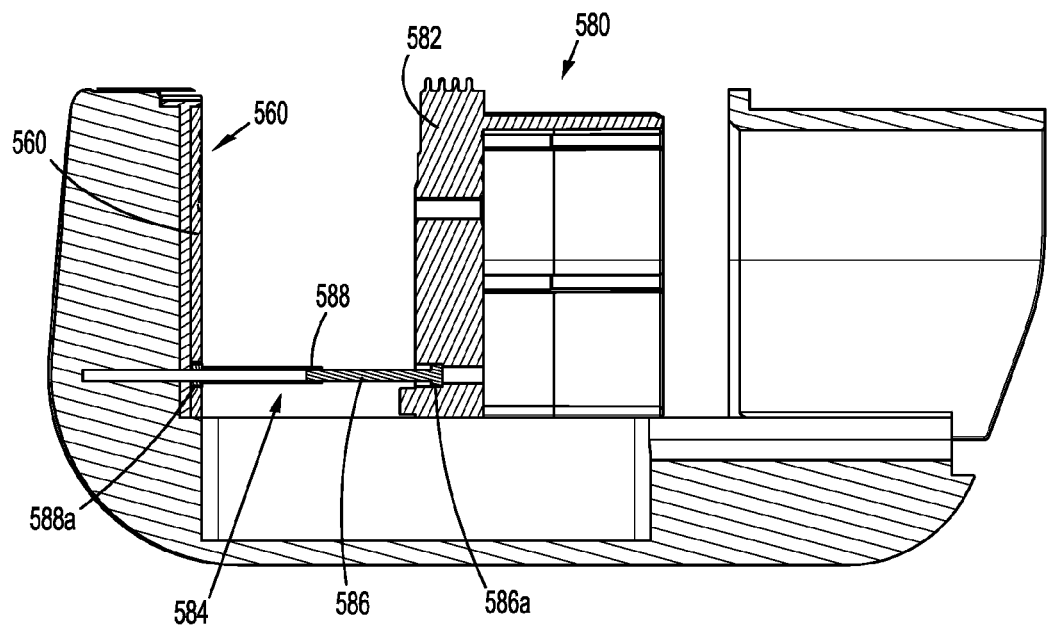
FIG. 20 is a cross-sectional side view of the end effector shown in FIG. 18 with the removable cartridge assembly in an open position.
Figure 21:
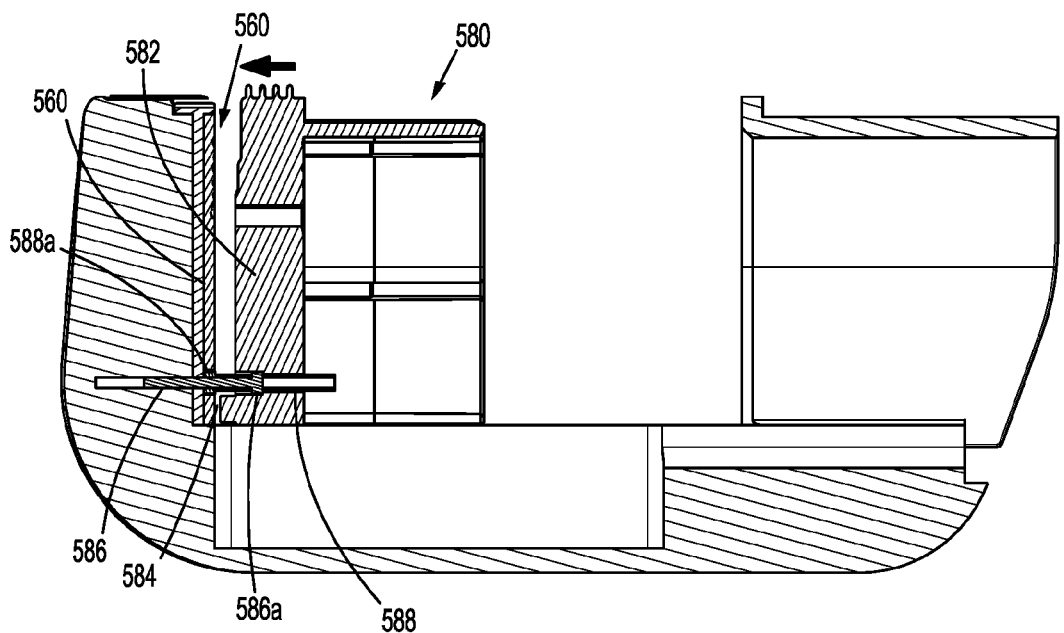
FIG. 21 is a cross-sectional side view of the end effector shown in FIG. 18 with the removable cartridge assembly in a closed position.
Figure 22:
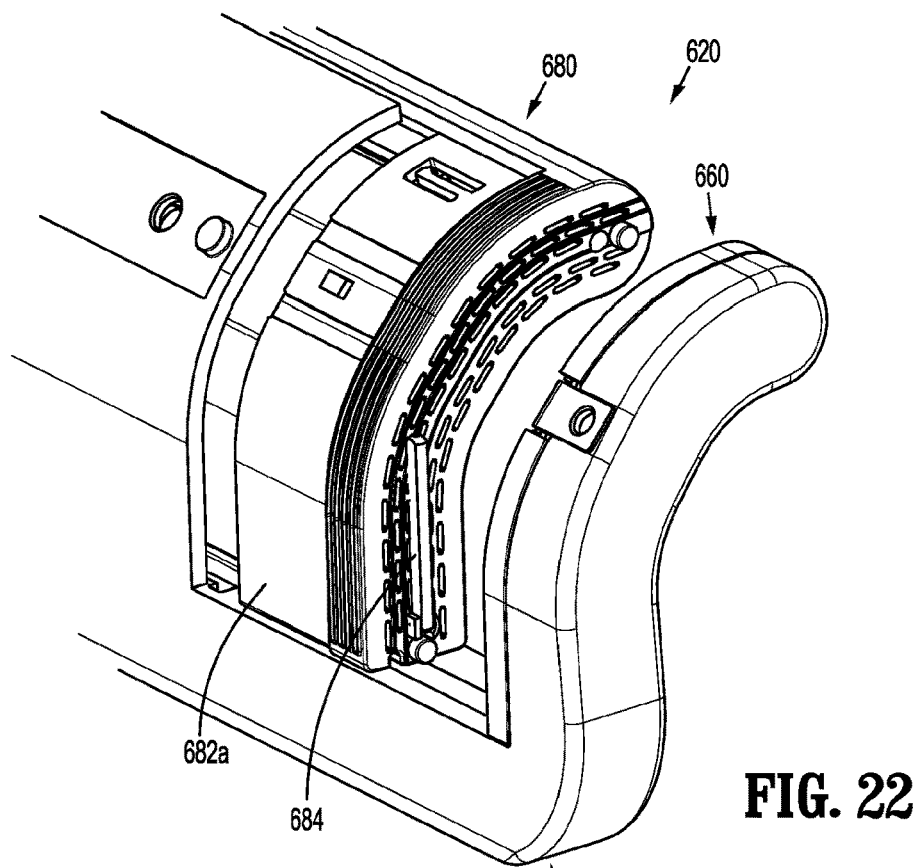
FIG. 22 is a perspective view of an end effector including a removable cartridge assembly having a tissue guide assembly according to another exemplary embodiment of the present disclosure with a tissue guide in an upright position.

With reference to FIGS. 16 and 17, in an alternative embodiment, a tissue guide assembly 484 includes a tissue guide member 484a that is separate or movable from a base 484b. A spring 484c received about a proximal portion of the tissue guide member 484a facilitates advancement of the tissue guide member 484a into engagement with an anvil assembly 460. More particularly, the tissue guide member 484a includes proximal and distal flanges 485a. 485b (FIG. 17). The spring 484c is disposed about the tissue guide 484a between the proximal and distal flanges 485a. 485b. The tissue guide member 484a is retained in a retracted position (not shown) by the base portion 482a of the replaceable cartridge assembly 480. When the replaceable cartridge assembly 480 is advanced during approximation of the replaceable cartridge assembly 480 relative to the anvil assembly 460, the spring 484c biases the tissue guide member 484a distally into engagement with the anvil assembly 460.

With reference now to FIGS. 18-21, in another embodiment of the present disclosure, a replaceable cartridge assembly 580 includes a tissue guide assembly 584. The tissue guide assembly 584 includes first and second telescoping members 586, 588. The first telescoping member 586 includes a proximal portion 586a that engages a body portion 582a of the replaceable cartridge assembly 580 and the second telescoping member 588 includes a distal portion 588a that engages an anvil assembly 560. The second telescoping member 588 defines a channel 587 (FIG. 19) through which the proximal portion 586a of the first telescoping member 586 is slidably disposed such that the first and second telescoping members 586, 588 can slide relative to one another during approximation and retraction of the replaceable cartridge assembly 580 relative to the anvil assembly 560. The tissue guide assembly 584 facilitates and maintains alignment of the replaceable cartridge assembly 580 relative to the anvil assembly 560 during operation of the stapling instrument 10 (FIG. 1).

Figure 23:
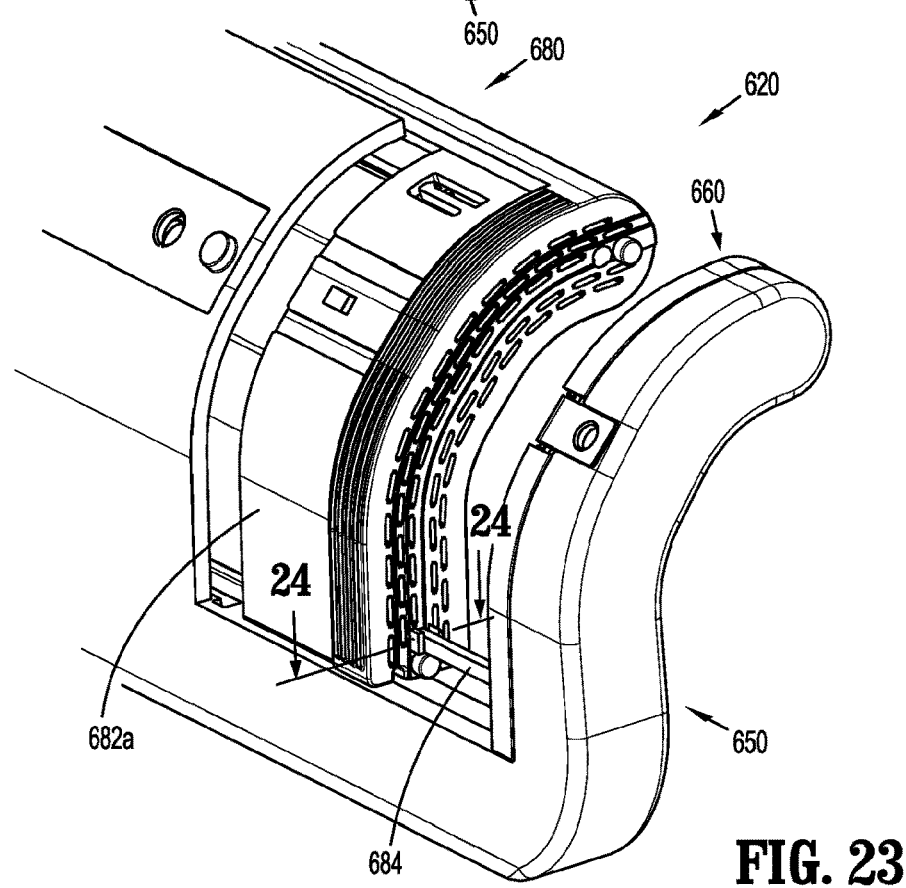
FIG. 23 is a perspective view of the end effector shown in FIG. 22 with the tissue guide in a pivoted position.

With reference to FIGS. 22-25, in yet another embodiment of the present disclosure, a replaceable cartridge assembly 680 includes a tissue guide member 684. The tissue guide member 684 is pivotally secured to a body portion 682a of the replaceable cartridge assembly 680 by a pivot member 684a (FIG. 25) and is moveable between a vertical position (FIG. 22) and a horizontal position (FIG. 23). The tissue guide member 684 is maintained in the vertical position during shipping and loading of the replaceable cartridge assembly 680 by a shipping cap (not shown). Upon loading of the replaceable cartridge assembly 680 within a frame assembly 650 of an end effector 620, and removal of the shipping cap, the tissue guide member 684 pivots from the vertical position to the horizontal position. In embodiments, the tissue guide member 684 is spring biased.

Figure 24:
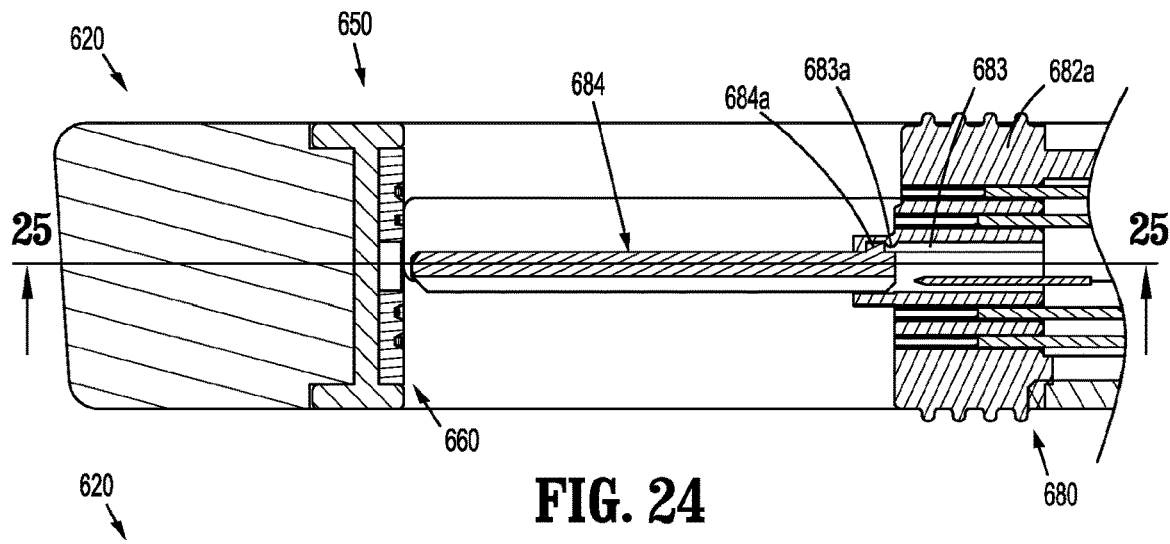
FIG. 24 is a cross-sectional view taken along line 24-24 shown in FIG. 23.
Figure 25:
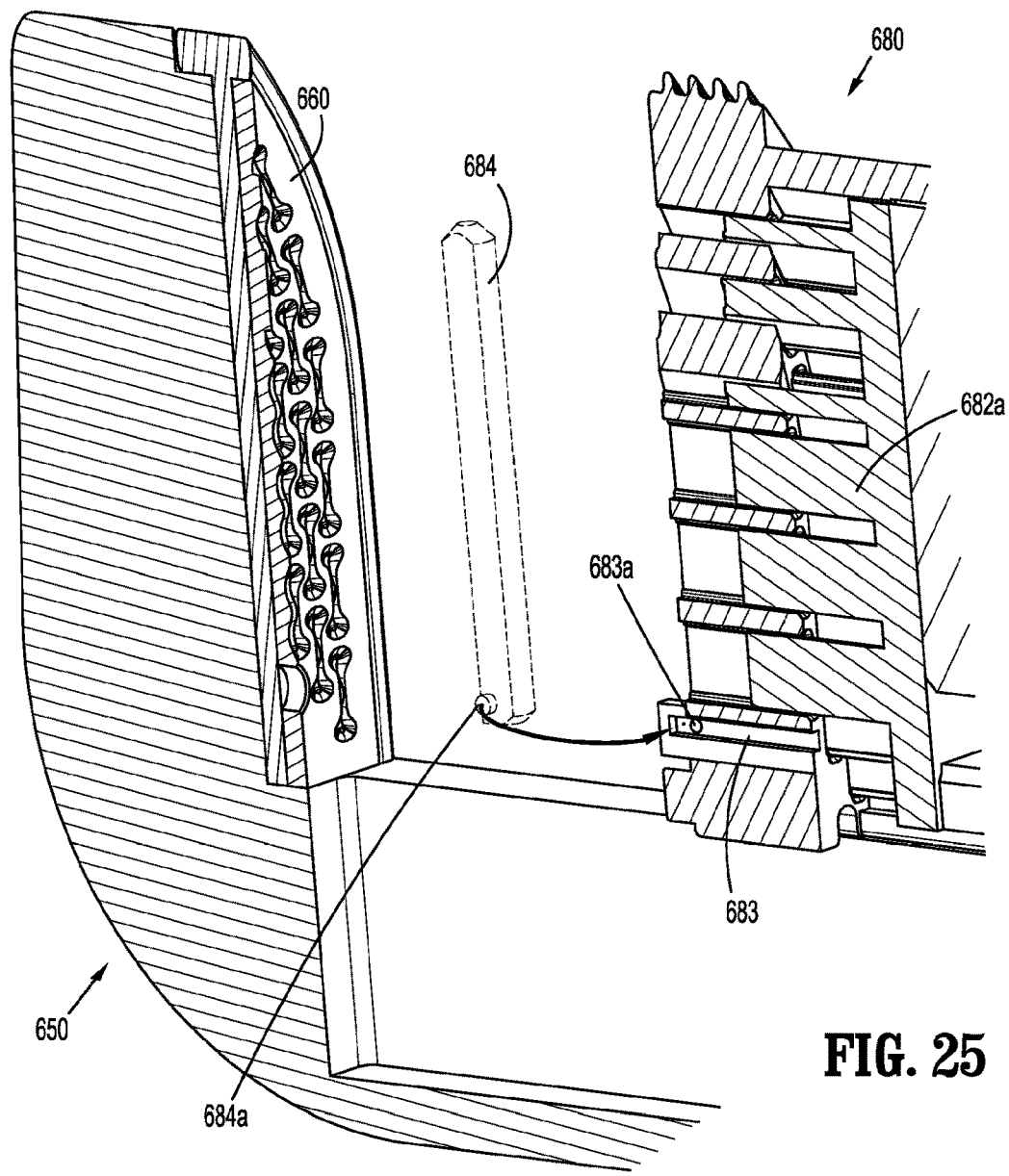
FIG. 25 is a cross-sectional view taken along line 25-25 shown in FIG. 24.

With particular reference to FIGS. 24 and 25, the pivot member 684a of the tissue guide member 684 is slidably received within a channel 683 in the body portion 682a of the replaceable cartridge assembly 680 and is releasably maintained in an advanced position by a bump 683a on the body portion 682a that extends into the channel 683. During approximation of the replaceable cartridge assembly 680 relative to an anvil assembly 660, the force of the pivot member 684a of the tissue guide member 684 against the bump 683a pushes the pivot member 684a over the bump 683a, thereby permitting the body portion 682a of the replaceable cartridge assembly 680 to advance over the tissue guide member 684 as the replaceable cartridge assembly is advanced to an approximated position (not shown).

Figure 26:
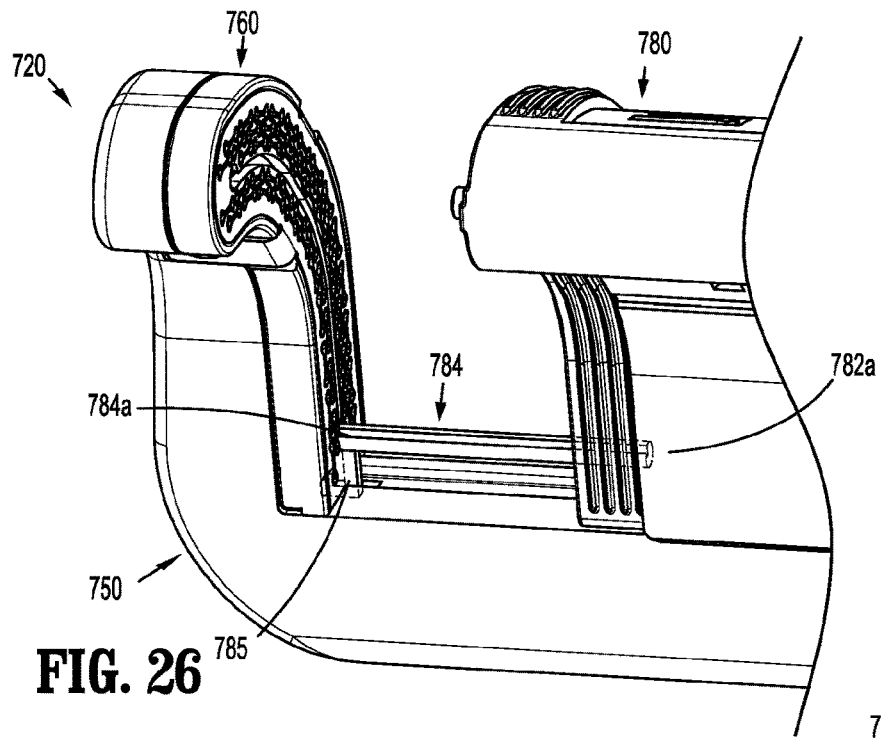
FIG. 26 is a perspective view of an end effector including a removable cartridge assembly and a tissue guide member according to yet another exemplary embodiment of the present disclosure.
Figure 27:
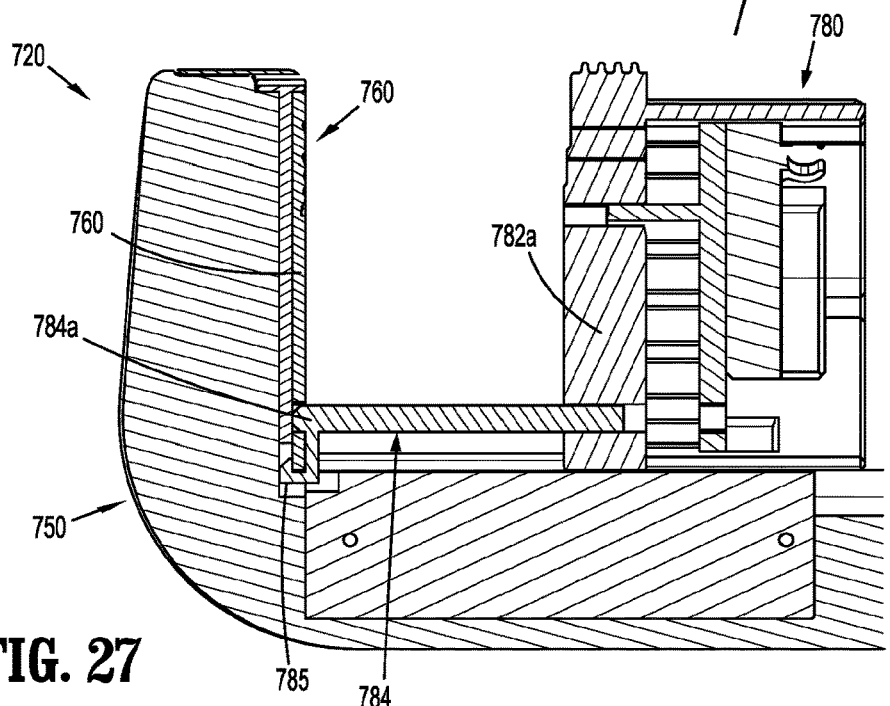
FIG. 27 is a cross-sectional side view of the end effector shown in FIG. 26.
Figure 28:
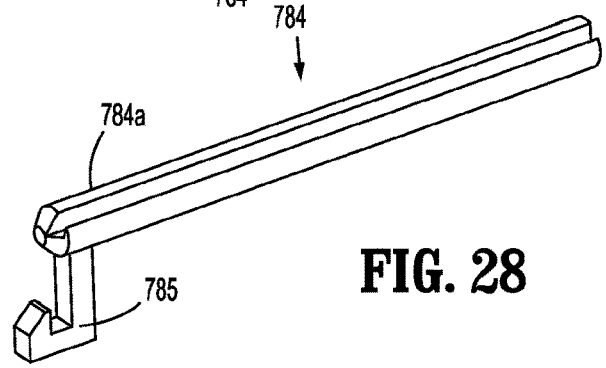
FIG. 28 is a perspective view of the tissue guide member shown in FIG. 26.
Figure 29:
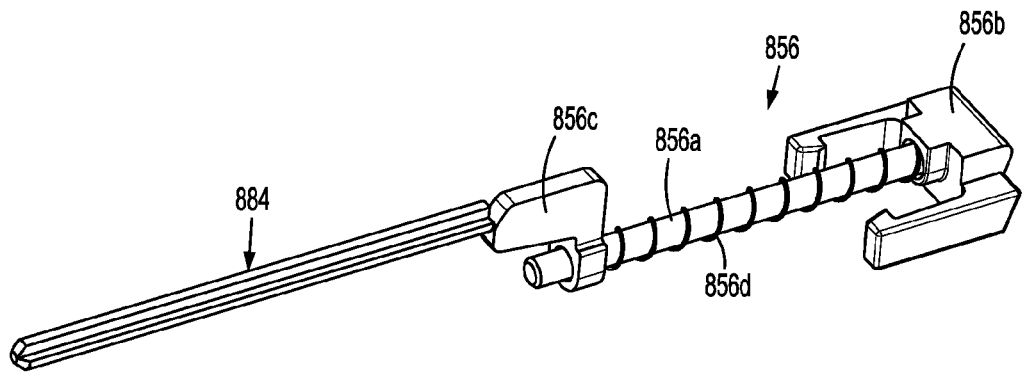
FIG. 29 is a perspective view of a tissue guide assembly according to another exemplary embodiment of the present disclosure.

Referring to FIGS. 26-28, in another embodiment of the present disclosure, an end effector 720 includes a replaceable cartridge assembly 780 having a tissue guide member 784. A distal portion 784a of the tissue guide member 784 includes a snap feature 785 for securing the tissue guide member 784 to an anvil assembly 760. During initial loading of the replaceable cartridge assembly 780 into a frame assembly 750 of the end effector 720, the snap feature 785 engages the anvil assembly 760 of the end effector 720. The tissue guide member 784 remains in an extended condition as the replaceable cartridge assembly 780 is slid proximally within the base portion 752 of the frame assembly 750 to its fully-loaded position, and during approximation and actuation of the end effector 720.

With reference to FIG. 29-32, in another yet another embodiment of the present disclosure, an end effector 820 (FIG. 30) includes a pusher assembly 856 for advancing a tissue guide member 884. The pusher assembly 856 includes a pusher pin 856a extending from a pusher base 856b, a pusher member 856c slidably mounted on about the pusher pin 856a, and a biasing member 856d (FIG. 29) received about the pusher pin 856a between the pusher member 856c and the pusher base 856b. The pusher base 856b secures the pusher assembly 856 within the base portion 852 of the frame assembly 850. The pusher member 856c is configured to engage the tissue guide member 884 of the replaceable cartridge assembly 880. The biasing member 856d is configured to bias the pusher member 856c distally.

Figure 30:
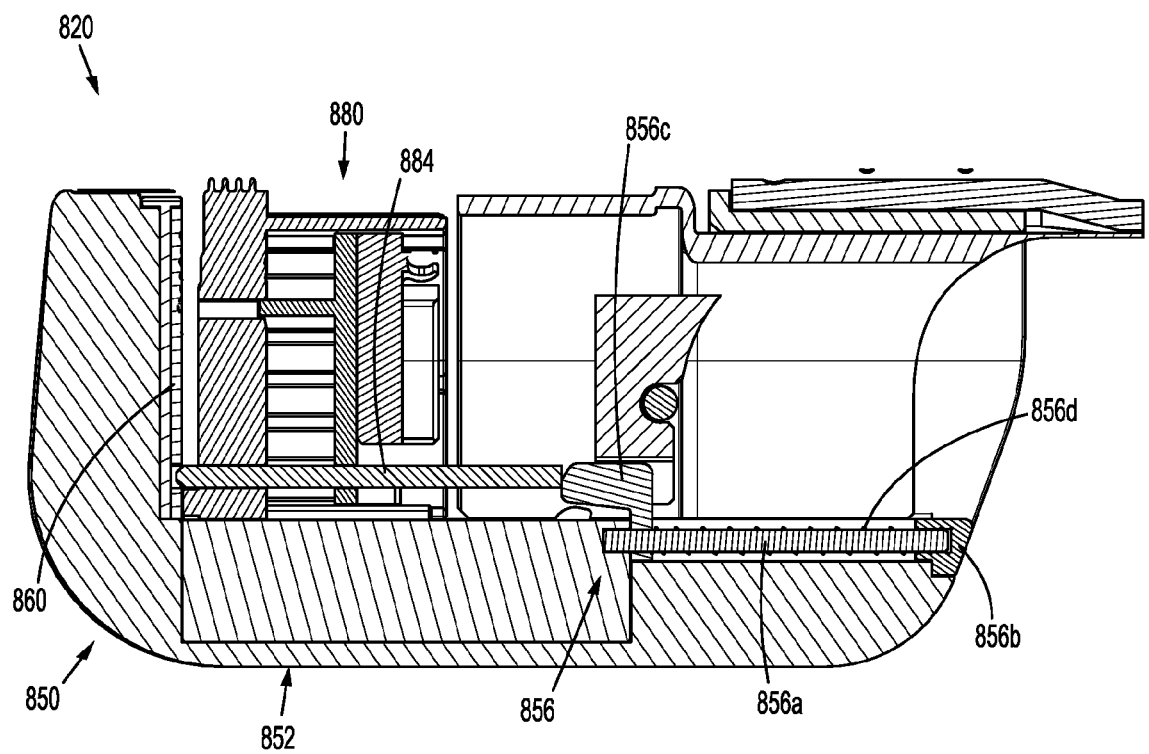
FIG. 30 is a cross-sectional side view of an end effector including a removable cartridge assembly and the tissue guide assembly shown in FIG. 29, with the removable cartridge assembly in a partially loaded condition.

With reference to FIG. 30, during initial loading of the replaceable cartridge assembly 880 within a frame assembly 850 of the end effector 820, a shipping cap (not shown) retains the tissue guide 884 within a body portion 882a of the replaceable cartridge assembly 880. A proximal end of the tissue guide 884 engages the pusher member 856c of the pusher assembly 856.

Figure 31:
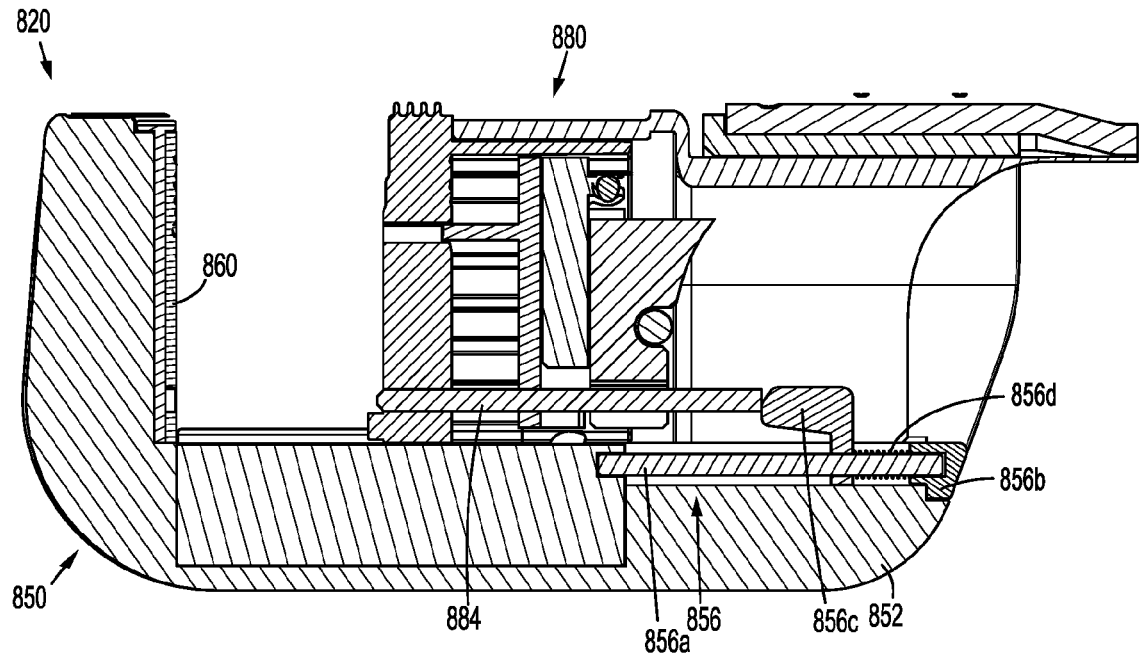
FIG. 31 is a cross-sectional side view of the end effector shown in FIG. 29, with the removable cartridge assembly in a fully loaded condition.

Turning to FIG. 31, as the replaceable cartridge assembly 880 is slid to the fully-loaded position, the tissue guide member 884 pushes the pusher member 856c proximally, thereby compressing the biasing member 856d.

Figure 32:
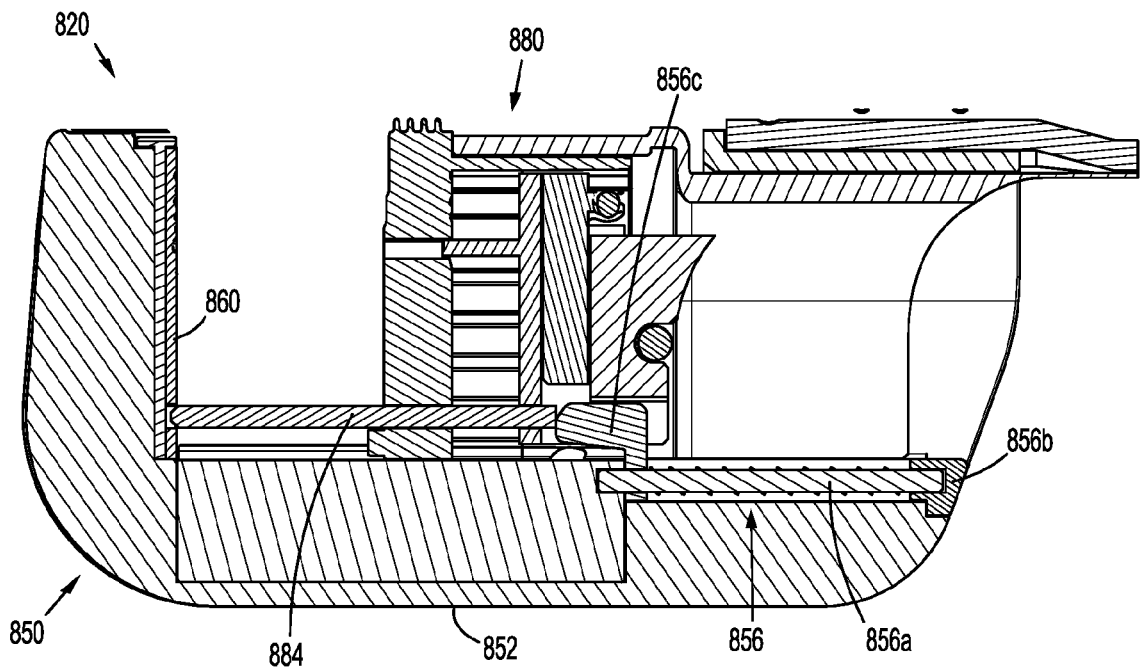
FIG. 32 is a cross-sectional side view of the end effector shown in FIG. 29, with the tissue guide assembly in an advanced position.

As shown in FIG. 32, after the shipping cap (not shown) is removed from the replaceable cartridge assembly 880, the tissue guide member 884 is advanced by the pusher member 856c, which is acted upon by the biasing member 856d, into engagement with the anvil assembly 860.

Figure 33:
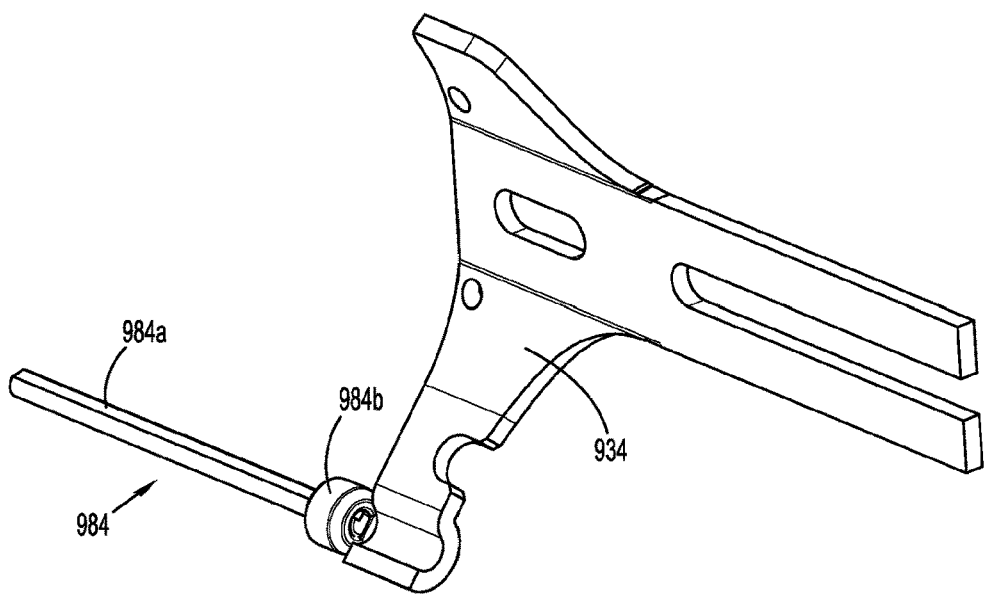
FIG. 33 is a perspective view of a tissue guide assembly and a distal end of a pusher member according to another exemplary embodiment of the present disclosure.
Figure 34:
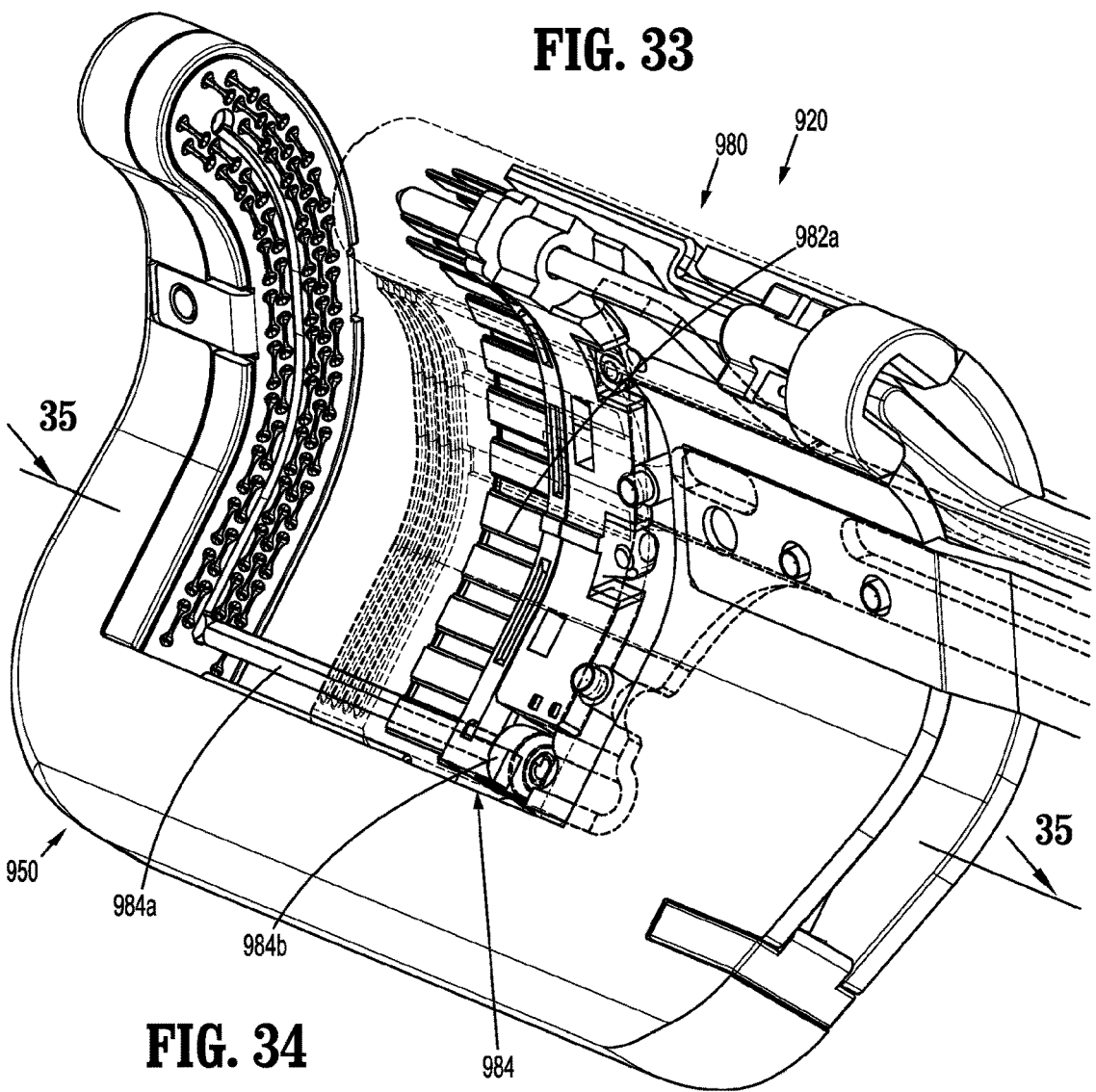
FIG. 34 is a perspective view of an end effector including the tissue guide assembly and pusher member shown in FIG. 33.
Figure 35:
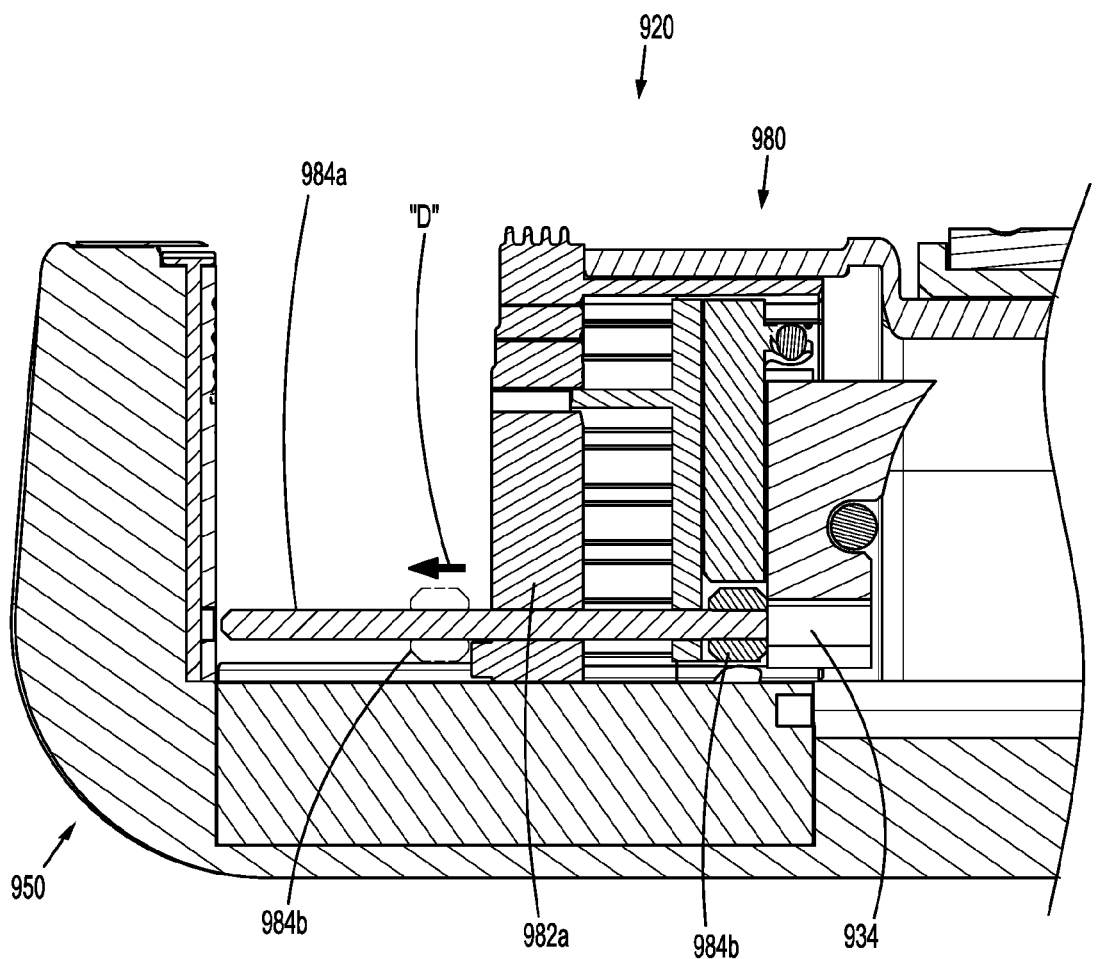
FIG. 35 is a cross-sectional side view taken along line 35-35 shown in FIG. 34.

Referring now to FIGS. 33-35, in still yet another embodiment of the present disclosure, an end effector 920 includes a replaceable cartridge assembly 980 having a tissue guide assembly 984. The tissue guide assembly 984 includes a tissue guide member 984a and a bushing 984b disposed on a proximal end of the tissue guide 984a. During initial or partial loading of the replaceable cartridge assembly 980 within a frame assembly 950 of the end effector 920, the tissue guide member 984a is retained within the body portion 982a of the replaceable cartridge assembly 980. As the replaceable cartridge assembly 980 is slid into a fully-loaded position, the bushing 984b on the proximal end of the tissue guide 984a engages a thrust bar 934 in the end effector 920, causing the tissue guide 984a to advance from within the body portion 982a of the replaceable cartridge assembly 980.

As illustrated in FIG. 35, during approximation and actuation of the replaceable cartridge assembly 980, the bushing 984b slides along the tissue guide member 984a, as indicated by arrow "D".

Figure 36:
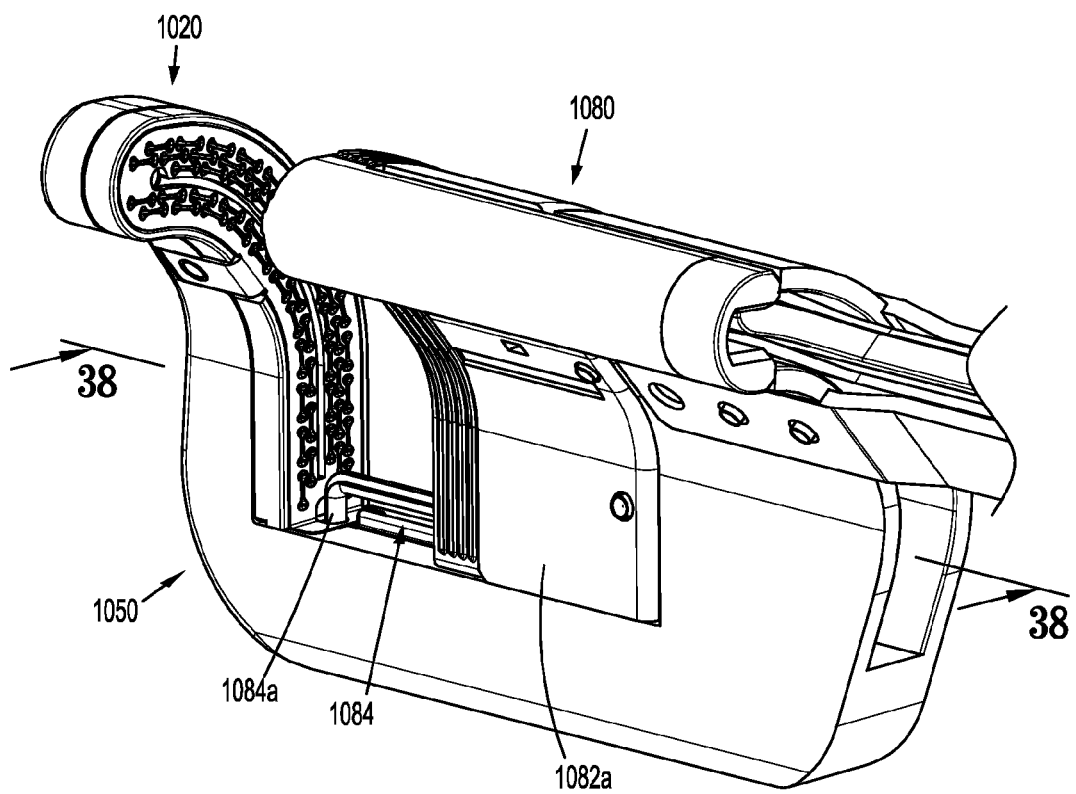
FIG. 36 is a perspective view of an end effector including a removable cartridge assembly having a tissue guide according to another exemplary embodiment of the present disclosure.
Figure 37:
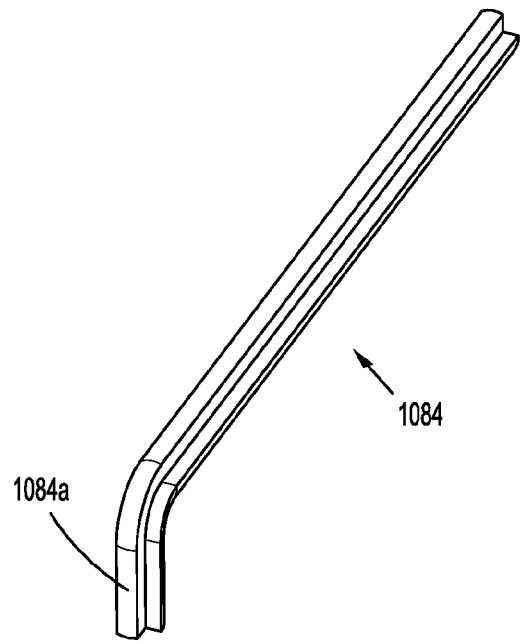
FIG. 37 is a perspective view of the tissue guide shown in FIG. 36.
Figure 38:
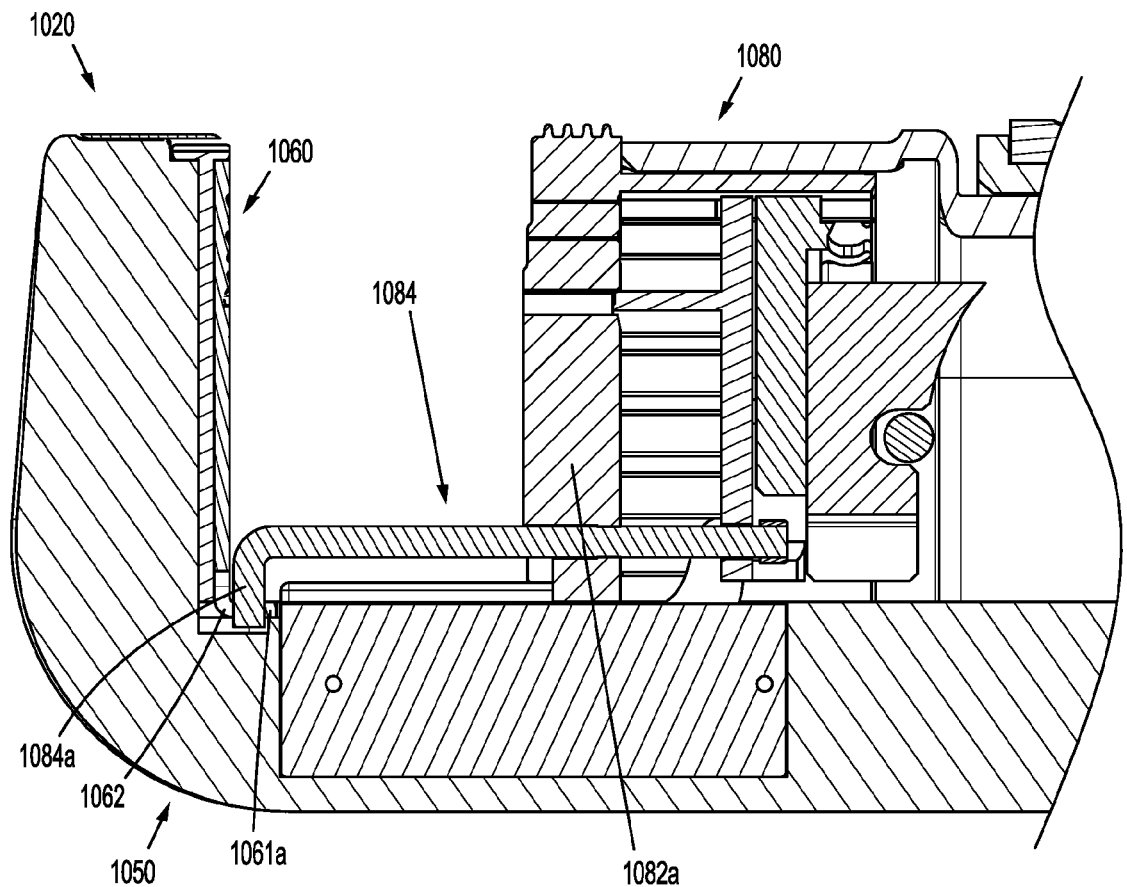
FIG. 38 is a cross-sectional side view taken along line 38-38 shown in FIG. 36.

With reference to FIGS. 36-38, in yet another embodiment of the present disclosure, a replaceable cartridge assembly 1080 includes a tissue guide member 1084 having a bent distal portion 1084a. During initial loading of the replaceable cartridge assembly 1080 within a frame assembly 1050 of the end effector 1020, the bent distal portion 1084a of the tissue guide member 1084 is received within an opening 1061 in a flange 1062 of the anvil assembly 1060. Alternatively. and/or in addition, the opening may be in the frame assembly 1050 of the end effector 1020. As the replaceable cartridge assembly 1080 is slid into the fully-loaded position, the tissue guide member 1084 is advanced from a body portion 1082a of the replaceable cartridge assembly 1080.

It will be understood that various modifications may be made to the embodiments disclosed herein. For example, the components of the surgical stapling instrument can be formed of any material suitable for surgical use and having the required strength characteristics. Therefore, the above description should not be construed as limiting, but merely as exemplifications of embodiments. Those skilled in the art will envision other modifications within the scope and spirit of the claims appended hereto.

The invention claimed is:

1. A surgical stapling instrument comprising:
an elongate body portion defining a longitudinal axis and having a proximal portion and a distal portion; and
an end effector supported on the distal portion of the elongated body portion, the end effector including:
a frame having a base portion and a jaw portion, the base portion being secured to the distal portion of the elongate body portion;
an anvil assembly supported on the jaw portion, the anvil assembly including an L-shaped protrusion fixedly mounted on an exterior surface of the anvil assembly and that extends proximally from the jaw portion towards the base portion of the frame of the end effector;
a cartridge assembly releasably supported on the base portion, the cartridge assembly including a housing and a tissue guide, the tissue guide moveable from a retracted position to an advanced position relative to the housing of the cartridge assembly; and
a pusher assembly disposed within the base portion of the frame of the end effector, the pusher assembly being configured to move the tissue guide from the retracted position to the advanced position such that the tissue guide engages the L-shaped protrusion of the anvil assembly to releasably retain the tissue guide in the advanced position.

2. The surgical stapling instrument of claim 1, wherein the tissue guide includes a tapered distal end surface.

3. The surgical stapling instrument of claim 1, wherein the tissue guide includes a notch that receives a portion of the L-shaped protrusion of the anvil assembly.

4. The surgical stapling instrument of claim 1, wherein the cartridge assembly further includes an alignment pin disposed within the housing of the cartridge assembly and moveable from a retracted position to an advanced position relative to the housing.

5. The surgical stapling instrument of claim 1, wherein the housing of the cartridge assembly defines a plurality of staple receiving pockets.

6. The surgical stapling instrument of claim 1, wherein the tissue guide includes a feature for maintaining a rotational orientation of the tissue guide relative to the housing of the cartridge assembly.

7. The surgical stapling instrument of claim 1, wherein tissue guide has a length and defines a longitudinal groove extending along the length of the tissue guide.

8. An end effector for a surgical stapling instrument, the end effector comprising:
a frame having a base portion and a jaw portion, the base portion configured to be secured to an elongate body portion of the surgical stapling instrument;
an anvil assembly supported on the jaw portion, the anvil assembly including an L-shaped protrusion fixedly mounted on an exterior surface of the anvil assembly and that extends proximally from the jaw portion towards the base portion of the frame of the end effector;
a cartridge assembly releasably supported on the base portion, the cartridge assembly including a housing and a tissue guide, the tissue guide moveable from a retracted position to an advanced position relative to the housing of the cartridge assembly such that the tissue guide engages the L-shaped protrusion of the anvil assembly to releasably retain the tissue guide in the advanced position; and
a pusher assembly disposed within the base portion, the pusher assembly being configured to move the tissue guide from the retracted position to the advanced position such that the tissue guide engages the anvil assembly.

9. The end effector of claim 8, wherein the tissue guide includes a tapered distal end surface.

10. The end effector of claim 8, wherein the L-shaped protrusion of the anvil assembly defines a notch that receives the tissue guide.

11. The end effector of claim 8, wherein the cartridge assembly further includes an alignment pin disposed within the housing of the cartridge assembly and moveable from a retracted position to an advanced position relative to the housing of the cartridge assembly.

12. The end effector of claim 8, wherein the housing of the cartridge assembly defines a plurality of staple receiving pockets.

13. The end effector of claim 8, wherein the tissue guide includes a feature for maintaining a rotational orientation of the tissue guide relative to the housing of the cartridge assembly.

14. The end effector of claim 8, wherein the tissue guide has a length and defines a longitudinal groove extending along the length of the tissue guide.

\* \* \* \* \*